US011608366B2

United States Patent
Kim et al.

(10) Patent No.: US 11,608,366 B2
(45) Date of Patent: Mar. 21, 2023

(54) RECOMBINANT VECTOR AND METHOD FOR PRODUCING RECOMBINANT FIBROBLAST GROWTH FACTOR 19 USING THE SAME

(71) Applicants: INDUSTRY FOUNDATION OF CHONNAM NATIONAL UNIVERSITY, Gwangju (KR); KOREA INSTITUTE OF OCEAN SCIENCE & TECHNOLOGY, Busan (KR)

(72) Inventors: Geun Joong Kim, Gwangju (KR); Hye Ji Choi, Jeollanam-do (KR); Dae Eun Cheong, Gwangju (KR); Su Kyoung Yoo, Gwangju (KR); Dong Hyun Lee, Gwangju (KR); Jae Hong Park, Gwangju (KR); Jung Hyun Lee, Busan (KR); Hyung Soon Yim, Seoul (KR); Young Jun An, Gyeonggi-do (KR); Kyeong Won Lee, Busan (KR)

(73) Assignees: INDUSTRY FOUNDATION OF CHONNAM NATIONAL UNIVERSITY, Gwangju (KR); KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 111 days.

(21) Appl. No.: 16/997,198

(22) Filed: Aug. 19, 2020

(65) Prior Publication Data
US 2021/0355182 A1    Nov. 18, 2021

(30) Foreign Application Priority Data
May 13, 2020   (KR) ........................ 10-2020-0057108

(51) Int. Cl.
| | | |
|---|---|---|
| C12N 15/70 | (2006.01) | |
| C07K 14/50 | (2006.01) | |
| A61K 38/00 | (2006.01) | |
| C12N 9/90  | (2006.01) | |

(52) U.S. Cl.
CPC .............. *C07K 14/50* (2013.01); *A61K 38/00* (2013.01); *C12N 9/90* (2013.01); *C12Y 503/04001* (2013.01)

(58) Field of Classification Search
None
See application file for complete search history.

(56) References Cited

U.S. PATENT DOCUMENTS 9,416,388 B2 * 8/2016 Ruddock .............. C12N 9/0083

FOREIGN PATENT DOCUMENTS

| KR | 10-2005-0009764 A | 1/2005 |
| KR | 10-1587433 B1 | 1/2016 |

OTHER PUBLICATIONS

Khambhati et al. (Frontiers in Bioeng. Biotech.7(248): 1-16, 2019).*
Mitra et al. (Research and Reports in Biochemistry 6: 57-65, 2016).*
Peter L.M. Jansen et al., "Pandora's Box Opens for Cholestatic Liver Disease", Hepatology, vol. 63, No. 3, pp. 694-696, 2016.
Bo Kong et al., "Soluble Expression of Disulfide Bond Containing Proteins FGF15 and FGF19 in the Cytoplasm of *Escherichia coli*", PLOS ONE, vol. 9, e85890, 2014.

* cited by examiner

*Primary Examiner* — Christine J Saoud
(74) *Attorney, Agent, or Firm* — Pleechae IP, LLC

(57) ABSTRACT

A recombinant vector according to an embodiment of the present invention may produce fibroblast growth factor 19 (FGF19) having enhanced solubility. The synonymous codon substitution variant fibroblast growth factor 19 (scvhFGF19) and chaperone ΔssDsbC may be simultaneously and independently expressed in a host cell into which the recombinant vector is introduced, thereby it is possible to overexpress the fibroblast growth factor 19 in a soluble state.

4 Claims, 8 Drawing Sheets
Specification includes a Sequence Listing.

RECOMBINANT VECTOR AND METHOD FOR PRODUCING RECOMBINANT FIBROBLAST GROWTH FACTOR 19 USING THE SAME

CROSS-REFERENCE TO RELATED APPLICATION AND CLAIM OF PRIORITY

This application claims priority to Korean Patent Applications No. 10-2020-0057108 filed on May 13, 2020 in the Korean Intellectual Property Office (KIPO), the entire disclosure of which is incorporated by reference herein.

BACKGROUND

1. Field of the Invention

The present invention relates to a recombinant vector and a method for producing recombinant fibroblast growth factor 19 using the same.

2. Description of the Related Art

Fibroblast growth factor (FGF) is a signaling protein which controls a wide range of biological functions including proliferation, survival and differentiation of a cell. 22 types of fibroblast growth factors are known up to the present, which are divided into three groups based on a mechanism of action, namely, paracrine, endocrine, and intracrine groups, and generally subdivided into seven subfamilies according to sequence similarity, biochemical function and evolutionary relationship. Recently, applicability of the growth factor as a therapeutic agent for treating various diseases including skin regeneration, revascularization, obesity, diabetes and cancer has been reported, studies on the mass production using these heterogeneous hosts such as yeast and E. coli have been continuously performed. However, only a small number of growth factors including FGF1 among 22 types of growth factors are expressed at a level that can be used for industrial use, and therefore it is difficult to observe distinct expression patterns in heterologous hosts with other fibroblast growth factors, or it is still in a level that it is difficult to expect practical use because they are expressed in an insoluble aggregate or a decomposed form without function.

FGF19, which belongs to endocrine growth factor, is also one of the fibroblast growth factors having properties difficult-to-express, and is known to be effective in treatments related nonalcoholic steatohepatitis, diabetes and obesity through control of cholesterol and bile acid synthesis in hepatocytes, and control of glucose and insulin in fat cells (Jansen, P. L., & Schaap, F. G. (2016); Hepatology, 63(3), 694-696). However, in the case of wild type hFGF19 having two disulfide bonds and amorphous structures at amino/carboxyl terminus, it is difficult to observe expression in E. coli or the growth factor is expressed in insoluble aggregates (called inclusion bodies).

Recently, there is a report that soluble expression of hFGF19 is implemented through a combination with an E. coli Shuffle T7 host which is improved so that a disulfide bond between cysteines in human fibroblast growth factor (hFGF19), in which thioredoxin (TRX) helpful for disulfide bond is fused to the amino terminus, and mouse fibroblast growth factor (known as mFGF15 in the case of the mouse) can be made in the cytoplasm (Kong, B., & Guo, G. L. (2014); PLoS One, 9(1), e85890). Given that recombinant hFGF19 is a medical protein for treatment of diseases, it is advantageous to produce hFGF19 without a possible change in amino acid thereof. However, the above paper proposes a separation of TRX and hFGF19 using a TEV protease recognition amino acid sequence, thereby it is difficult to remove a fusion partner without addition of amino acid to the amino terminus of hFGF19, as well as the yield is decreased progressively from 2 mg/L to 0.5 mg/L due to the time required for processing and inappropriate cutting with expensive proteases, and aggregation of hFGF19 results from the cutting process. Therefore, a need to solve immunogenic problems caused by the added amino acid and to improve the yield through independent expression of a target protein still exist in the art.

In order to solve the above-described problems, advanced research has been conducted based on Korean Patent No. 10-1587433, which proposes a method capable of improving the expression pattern of a recombinant protein by adjusting a translation rate without utilizing the fusion partner, wherein preparation and screening of a scvhFGF19 library, in which ten amino acid codons in a 5'-end region of polynucleotide encoding hFGF19 are substituted with synonymous codons. As a result, only scvhFGF19 variants with a significantly increased expression level compared to wild type hFGF19 of which expression could not be observed in SDS-PAGE were screened, and scvhFGF19 variants with an increased soluble expression ratio were not screened. This result demonstrates that it is difficult to completely solve the problem of inappropriate folding due to inherent structural characteristics of hFGF19, for example, the amorphous structure appearing at the amino/carboxyl terminus and two disulfide bonds, by merely adjusting the translation rate through synonymous codon substitution. Therefore, there is an urgent need to develop a solution for these problems.

SUMMARY

It is an object of the present invention to provide a recombinant vector which increases soluble expression of fibroblast growth factor 19 without utilizing a fusion partner.

Another object of the present invention is to provide a method for producing recombinant fibroblast growth factor 19 using the recombinant vector.

To achieve the above objects, the following technical solutions are adopted in the present invention.

1. A recombinant vector for producing fibroblast growth factor 19 (FGF19) having enhanced solubility, the recombinant vector including: a first polynucleotide which encodes the fibroblast growth factor 19 (FGF19); and a second polynucleotide which encodes disulfide bond isomerase (DsbC).

2. The recombinant vector according to above 1, wherein the fibroblast growth factor 19 is human fibroblast growth factor 19.

3. The recombinant vector according to above 1, wherein the first polynucleotide encodes a protein consisting of an amino acid sequence of SEQ ID NO: 1.

4. The recombinant vector according to above 1, wherein, in the first polynucleotide, any one or more of 10 codons in a 5' end coding region except for an initiation codon in polynucleotide consisting of a sequence of SEQ ID NO: 5 is a synonymous codon.

5. The recombinant vector according to above 1, wherein the second polynucleotide encodes a protein consisting of an amino acid sequence of SEQ ID NO: 2.

6. The recombinant vector according to above 1, wherein the second polynucleotide does not include a signal sequence.

7. The recombinant vector according to above 1, wherein the first polynucleotide consists of a sequence of SEQ ID NO: 3, and the second polynucleotide consists of a sequence of SEQ ID NO: 4.

8. The recombinant vector according to above 1, wherein the first polynucleotide and the second polynucleotide are operably linked to different promoters, respectively.

9. A method for producing recombinant fibroblast growth factor 19 using the recombinant vector according to any one of above 1 to 8.

10. The method according to above 9, wherein the method is performed by cell-free protein synthesis (CFPS).

11. The method according to above 9, including culturing a host cell transformed with the recombinant vector.

12. The method according to above 11, wherein the host cell is *Escherichia coli*.

13. Recombinant fibroblast growth factor 19 having enhanced solubility produced by the method according to any one of above 9 to 12.

14. A pharmaceutical composition for treating diabetes or cancer, including the recombinant fibroblast growth factor 19 according to above 13.

15. A composition for skin regeneration, revascularization, or antiobesity, including the recombinant fibroblast growth factor 19 according to above 13.

The present invention provides a recombinant vector and a method for producing recombinant fibroblast growth factor 19 using the same. According to the present invention, the synonymous codon substitution variant fibroblast growth factor 19 (scvhFGF19) and chaperone ΔssDsbC are simultaneously and independently expressed in a host cell into which the recombinant vector is introduced, thereby it is possible to overexpress the fibroblast growth factor 19 in a soluble state, due to when not utilizing tags such as an existing fusion partner there is no change in the amino acid, which is a problem generated in the removal process.

BRIEF DESCRIPTION OF THE DRAWINGS

The above and other objects, features and other advantages of the present invention will be more clearly understood from the following detailed description taken in conjunction with the accompanying drawings, in which:

FIG. 2 illustrates a corresponding wobble base to transform ten amino acid codons in a 5' end coding region except for an initiation codon of FGF19 into synonymous codons, and illustrates that fluorescent protein mCherry for screening variants is fused to a carboxyl terminus to be expressed;

Figure 3:
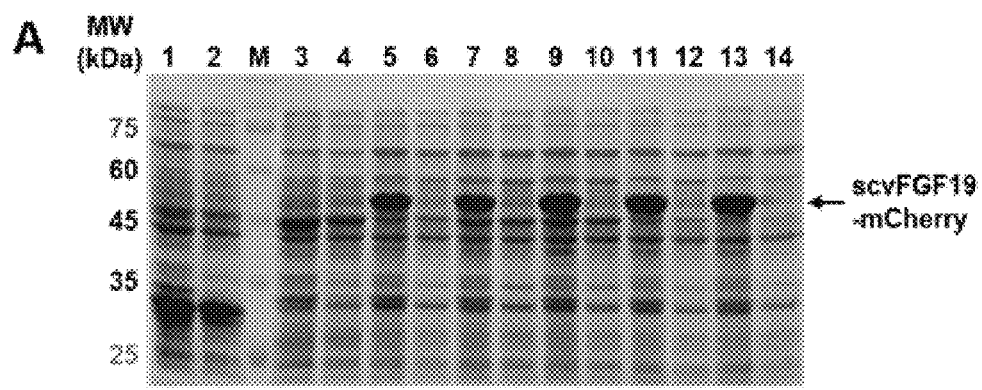
FIG. 3 is images illustrating results obtained by analyzing expression patterns of a synonymous codon substitution variant protein of the screened fibroblast growth factor 19. A of FIG. 3 is an image illustrating an expression pattern in *E. coli* host XL1-Blue, B of FIG. 3 is an image illustrating results obtained by comparing and analyzing the expression patterns in *E. coli* host XL1-Blue and Origami 2, and C of FIG. 3 is an image illustrating an expression pattern when scvhFGF19 was expressed alone in Origami 2 after removing reporter mCherry used for screening.
Figure 3:
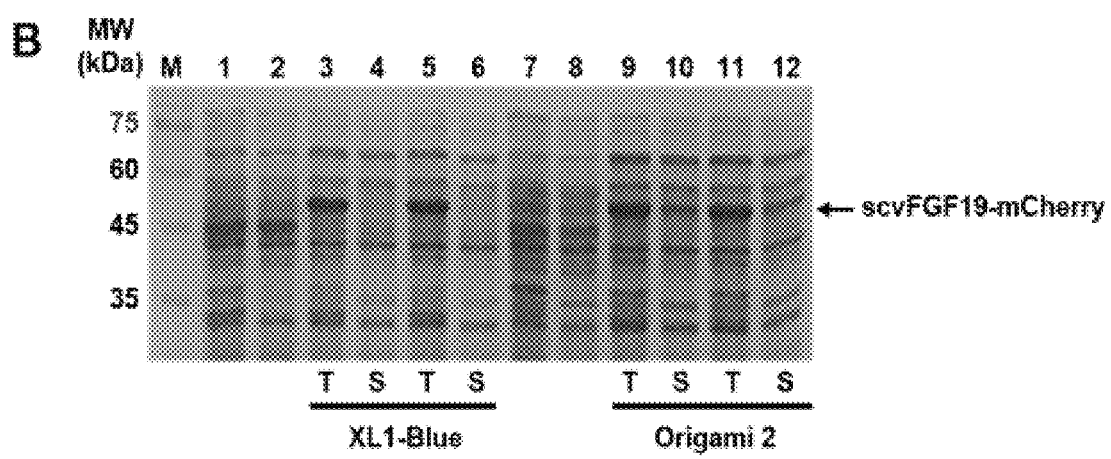
Figure 3:
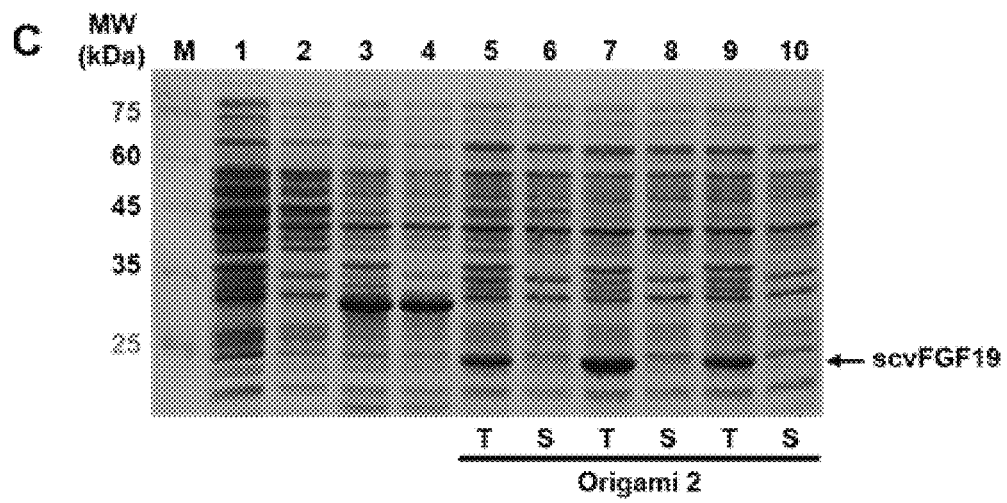
Figure 4:
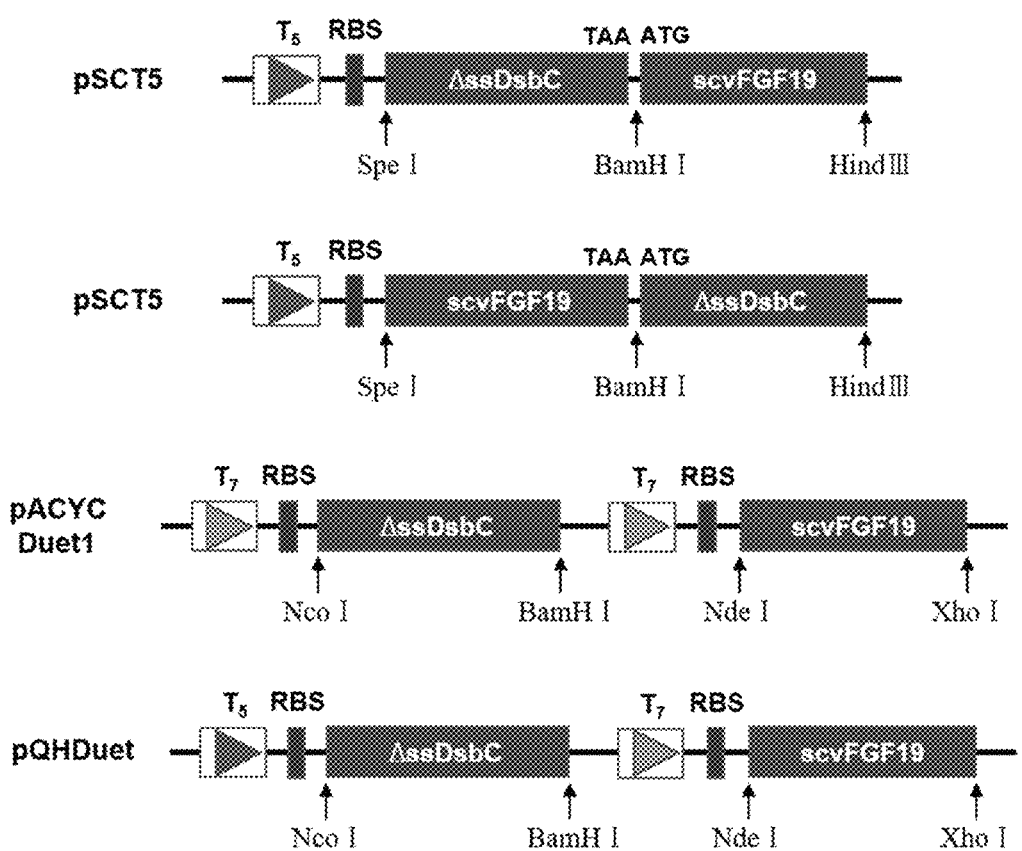
Figure 5:
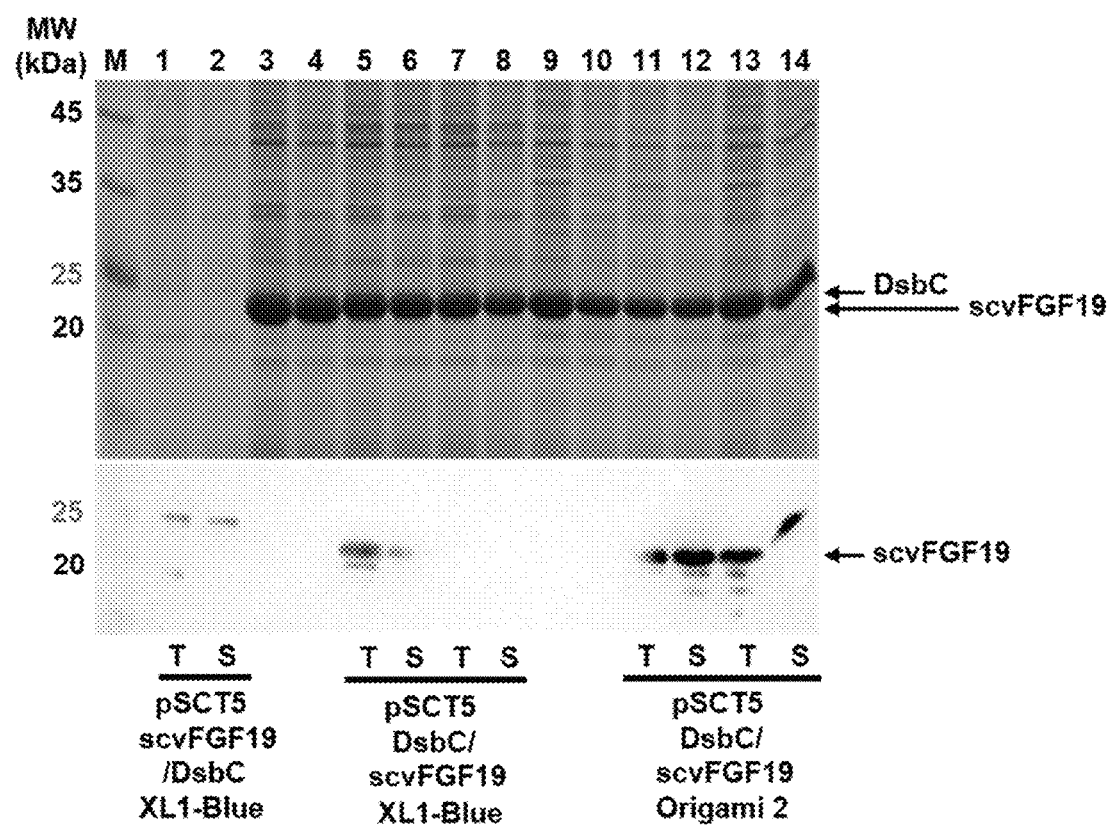
Figure 6:
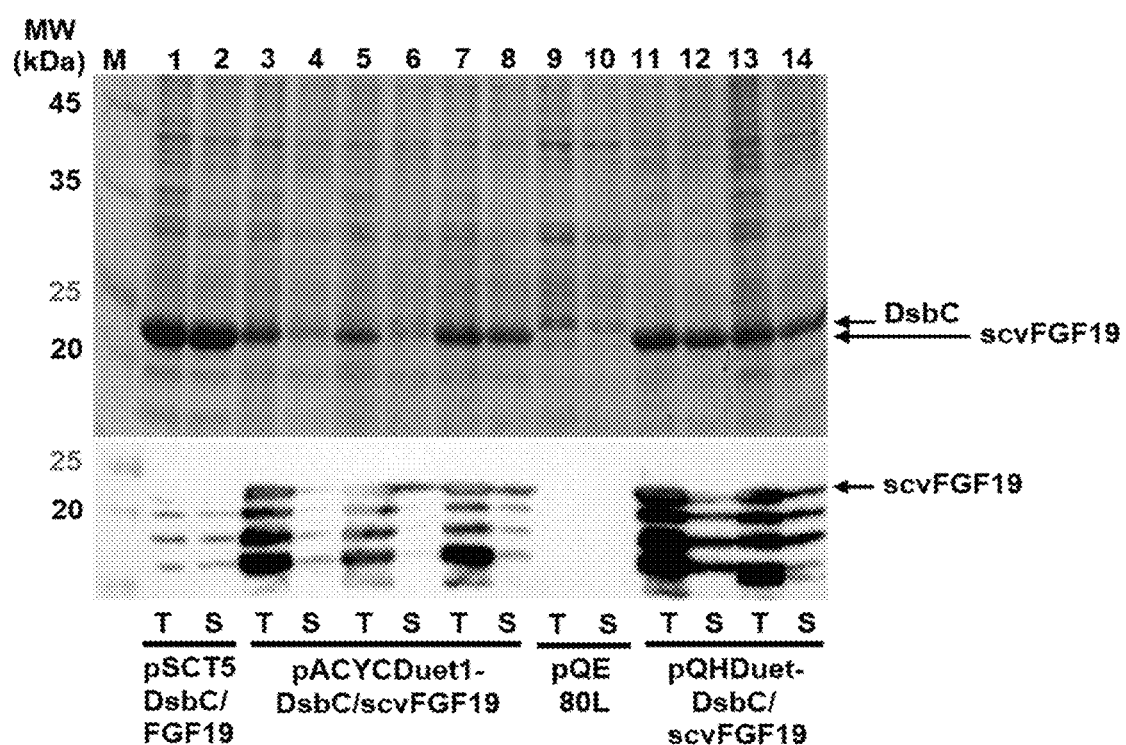
Figure 7:
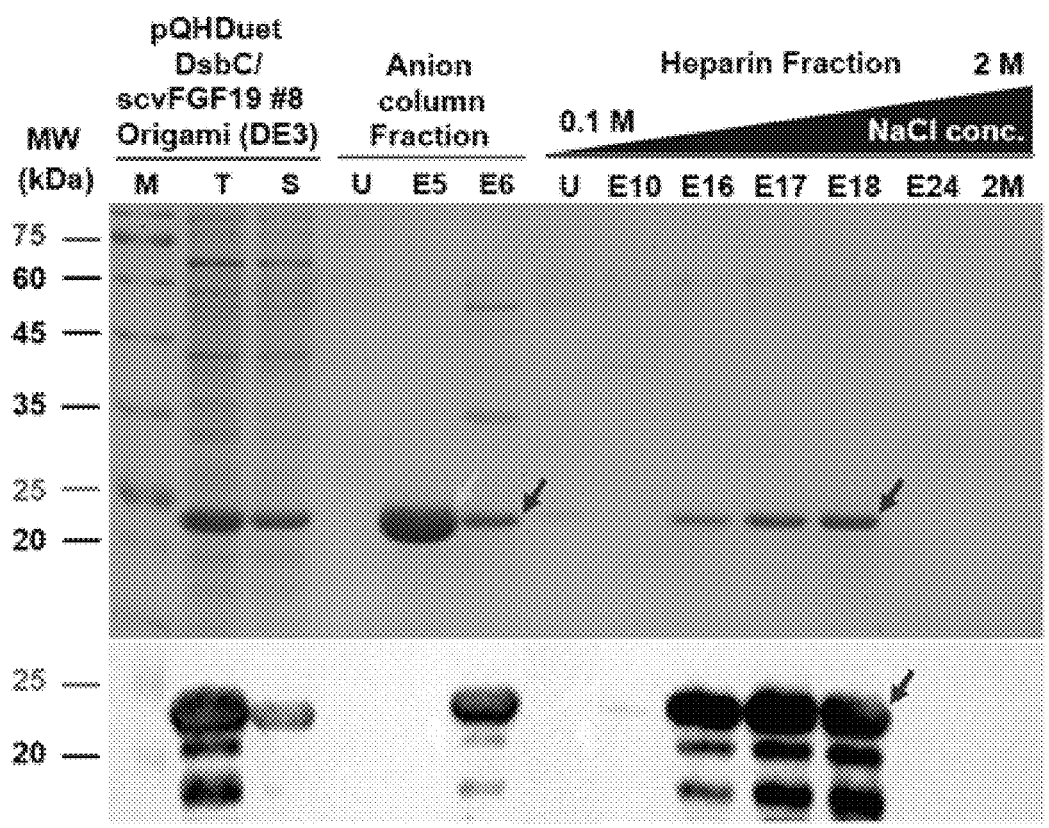
Figure 8:
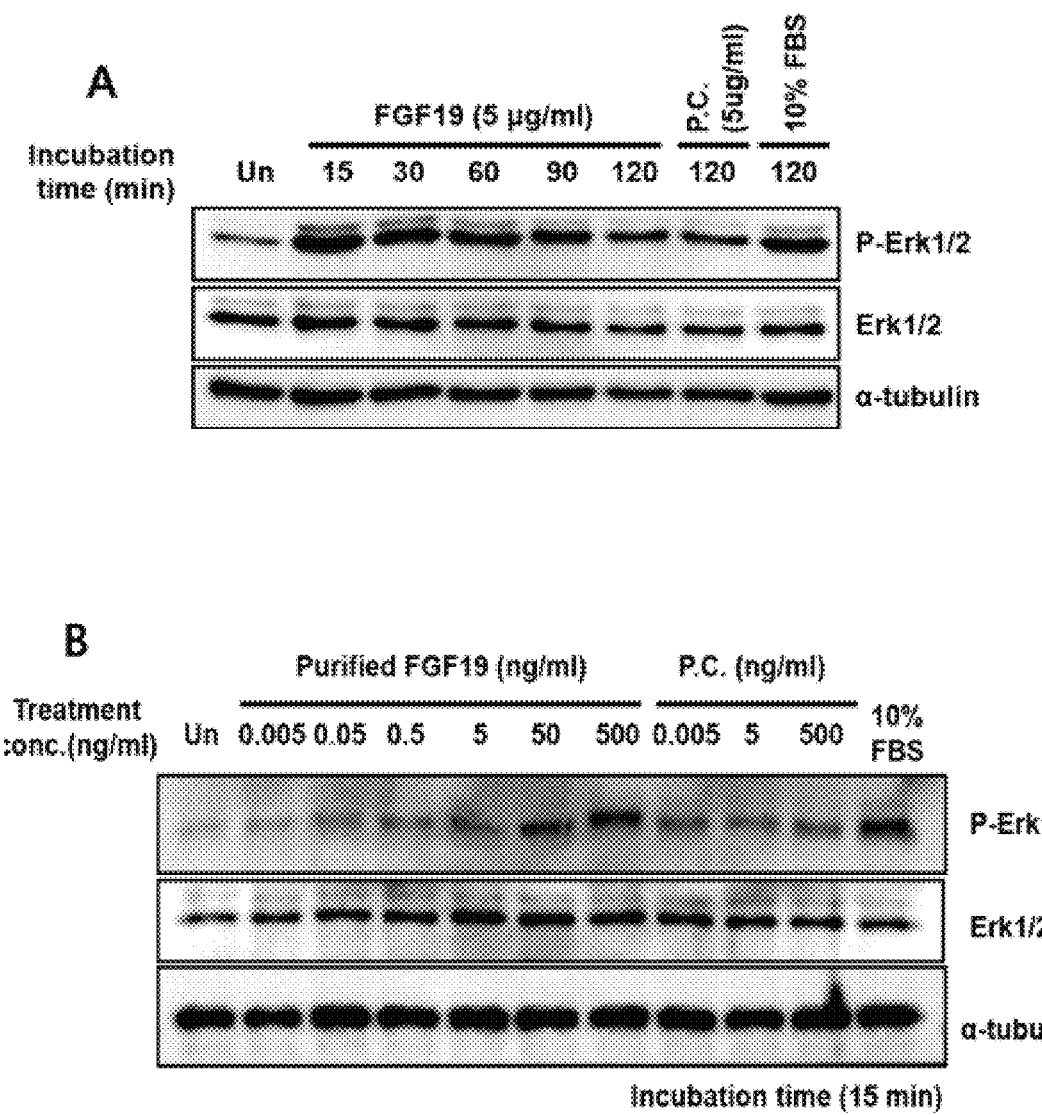

In A of FIG. 3, M is a molecular weight size marker, lanes 1 and 2 are total and soluble protein fractions expressing pSCT5_mCherry empty vector before the insertion of scvhFGF19 as a control, lanes 3 and 4 are total and soluble protein fractions of *E. coli* XL1-Blue in which plasmid is not transformed, lanes 5, 7, 9, 11 and 13 are total protein fractions of the screened synonymous codon substitution variant scvhFGF19-mCherry, and lanes 6, 8, 10, 12 and 14 are soluble fractions of scvhFGF19;

In B of FIG. 3, M is the molecular weight size marker, lanes 1 and 2 are soluble protein fractions of *E. coli* XL1-Blue in which plasmid is not transformed as a control, lanes 3 to 6 are total and soluble protein fractions in which final screened synonymous codon substitution variant scvhFGF19-mCherry is expressed in XL1-Blue, lanes 7 and 8 are total and soluble protein fractions of *E. coli* Origami 2 in which plasmid is not transformed, and lanes 9 to 12 are total and soluble protein fractions in which the final screened synonymous codon substitution variant scvhFGF19-mCherry is expressed in Origami 2;

In C of FIG. 3, M is the molecular weight size marker, lanes 1 and 2 are total and soluble protein of *E. coli* Origami 2 in which plasmid is not transformed as a control, lanes 3 and 4 are total and soluble proteins of Origami 2 having pSCT5 mCherry empty vector as a control, and lanes 5 to 10 are total and soluble protein fractions in which scvhFGF19 is expressed alone in *E. coli* Origami 2 strain;

FIG. 4 is a schematic diagram illustrating various plasmids designed to simultaneously express chaperone ΔssDsbC for increasing solubility of the synonymous codon substitution variant human fibroblast growth factor 19 (scvhFGF19);

FIG. 5 is an image illustrating results obtained by analyzing the expression pattern of scvhFGF19 according to relative cloning positions of DsbC by SDS-PAGE and western blotting;

In FIG. 5, lanes 1 and 2 are total and soluble fractions of *E. coli* XL1-Blue having pSCT5_scvhFGF19/ΔssDsbC, lanes 5 to 8 are total and soluble fractions of *E. coli* XL1-Blue having pSCT5_ΔssDsbc/scvhFGF19, and lanes 11 to 14 are total and soluble fractions of *E. coli* Origami 2 having pSCT5_ΔssDsbC/scvhFGF19, which are results obtained by analyzing the fractions;

FIG. 6 is an image illustrating results of SDS-PAGE and western blotting analyses when ΔssDsbC and scvhFGF19 were simultaneously expressed in Origami (DE3) using the above prepared expression system;

In FIG. 6, lanes 1 and 2 are total and soluble fractions of *E. coli* Origami 2 having pSCT5_ΔssDsbc/scvhFGF19, lanes 3 to 8 are total and soluble fractions of *E. coli* Origami (DE3) having pACYCDuet1_ΔssDsbC/scvhFGF19, and lanes 11 to 14 are total and soluble fractions of *E. coli* Origami (DE3) having pQHDuet_ΔssDsbC/scvhFGF19, which are results obtained by analyzing the fractions;

FIG. 7 an image illustrating results obtained by expressing pQHDuet_ΔssDsbC/scvhFGF19 capable of independently and simultaneously expressing ΔssDsbC and scvhFGF19 in *E. coli* Origami (DE3), and then purifying scvhFGF19 utilizing anion exchange chromatography and heparin-affinity chromatography;

FIG. 8 is images illustrating results obtained by evaluating activity of synonymous codon substitution variant human fibroblast growth factor 19 (scvhFGF19) which is prepared by the recombinant expression vector according to the present invention in a human hepatocellular carcinoma cell line (HepG2 cell) and purified by the two-step chromatography through phosphorylation of ERK; and A of FIG. 8 is a result obtained by confirming the phosphorylation level of ERK1/2 over time after treating scvhFGF19 at a fixed concentration, and B of FIG. 8 is a result obtained by analyzing the ERK1/2 phosphorylation level after treating scvhFGF19 at various concentrations for a certain period of time.

DETAILED DESCRIPTION

Hereinafter, the present invention will be described in detail.

The present invention provides a recombinant vector for producing fibroblast growth factor 19 (FGF19) having enhanced solubility, wherein the recombinant vector includes a first polynucleotide which encodes the fibroblast growth factor 19 (FGF19), and a second polynucleotide which encodes disulfide bond isomerase (DsbC).

The fibroblast growth factor 19 is not particularly limited in terms of its origin. For example, the fibroblast growth factor 19 may be human fibroblast growth factor 19 consisting of an amino acid sequence of SEQ ID NO: 1.

The fibroblast growth factor 19 is fibroblast growth factor 19 encoded from polynucleotide substituted with a synonymous codon.

The first polynucleotide is not particularly limited so long as it encodes a protein consisting of the amino acid sequence of SEQ ID NO: 1.

In the first polynucleotide, any one or more of first 10 codons except for an initiation codon in a 5' end coding region in polynucleotide consisting of a sequence of SEQ ID NO: 5 may be the synonymous codon.

The synonymous codon substitution causes only the wobble codon of ten amino acids in the 5' end coding region except for the initiation codon of FGF19 to be substituted, and may have the same codon as wild type FGF19 or may be substituted with one or more other codons.

For example, the first polynucleotide may have a form in which eight codons are substituted, and specifically, may consist of a sequence of SEQ ID NO: 3, but it is not limited thereto.

The disulfide isomerase (DsbC) may be expressed in the cytoplasm to induce disulfide bond formation of the fibroblast growth factor 19 protein.

The second polynucleotide is not particularly limited so long as it encodes a protein consisting of an amino acid sequence of SEQ ID NO: 2.

The second polynucleotide may not include a signal sequence, for example, may consist of a sequence of SEQ ID NO: 4.

The first polynucleotide may consist of the sequence of SEQ ID NO: 3, and the second polynucleotide may consist of the sequence of SEQ ID NO: 4.

The first polynucleotide and the second polynucleotide are operably linked to a promoter.

As used herein, the term "operably linked" means a state in which a sequence for control of nucleic acid expression and the target protein or a nucleic acid sequence encoding RNA are functionally linked so as to perform a general function. For example, the promoter and the protein or the nucleic acid sequence encoding RNA may be operably linked to affect the expression of the coding sequence. Operable linkage with the expression vector may be made using genetic recombination techniques well known in the art, and site-specific DNA cleavage and linkage may be performed using enzymes and the like generally known in the art.

The first polynucleotide and the second polynucleotide may be operably linked to one promoter or may be operably linked to separate promoters, respectively.

When the first polynucleotide and the second polynucleotide are operably linked to one promoter, a position relative to the promoter is not limited, but it is preferable that the promoter—the second polynucleotide—the first polynucleotide are linked in this order.

When the first polynucleotide and the second polynucleotide are operably linked to separate promoters, respectively, the promoters may be the same as or different from each other.

When the first polynucleotide and the second polynucleotide are operably linked to different promoters, soluble expression of the target protein may be further enhanced.

The promoter may be derived from a target for introducing the recombinant vector of the present invention, and the type thereof is not limited. For example, the promoter may be a T5 promoter or a T7 promoter.

In the host cell into which the recombinant vector of the present invention is introduced, DsbC protein and synonymous codon substitution variant fibroblast growth factor 19 (scvhFGF19) may be independently and simultaneously expressed.

The recombinant vector of the present invention may use a plasmid vector, a cosmid vector, a bacteriophage vector, a viral vector, and the like as a template, but it is not limited thereto. Suitable recombinant vectors may include expression control elements such as a promoter, operator, initiation codon, termination codon, polyadenylation signal, enhancer, and the like, and may be variously prepared according to the purposes.

The recombinant vector may include an antibiotic resistance marker for screening the host into which the vector is introduced, which may be either inherent in the vector or introduced externally.

The present invention provides a method for producing recombinant fibroblast growth factor 19 using the recombinant vector.

The above-described method may be performed by conventional methods known in the art, for example, may be performed by cell-free protein synthesis (CFPS).

Specifically, the recombinant vector may be contained in a composition including a cell extract related to protein synthesis, nucleic acid, amino acid, energy source, buffer solution and the like.

The cell extract may be ribosomes, etc., and may be extracted from *E. coli*, yeast, plant and animal cells, and may be appropriately selected according to the type of protein to be produced.

The above-described method may include the step of culturing a host cell transformed with the recombinant vector.

The host cell may be used to express the fibroblast growth factor 19 and disulfide bond isomerase by introducing the recombinant vector of the present invention therein.

The host cell is not particularly limited, and may be, for example, strains of genus *Escherichia*, genus *Salmonella*, genus *Shigella*, genus *Enterobacter*, genus *Proteus*, genus *Pseudomonas*, genus *Moraxella*, genus *Helicobacter*, genus *Stenotrophomonas*, genus *Bdellovibrio*, genus *Legionella*, genus *Neisseria*, and *Erwinia*, etc., and specifically, *Escherichia coli*.

The transformation may be performed by conventional methods known in the art, and may be introduced, for example, through a natural introduction method, thermal shock method, electric shock method, or the like, but it is not particularly limited thereto.

The host cell may overexpress hFGF19 and express DsbC in the cytoplasm, thereby producing recombinant hFGF19 having enhanced soluble expression.

Conditions for culturing the host cell are not particularly limited. For example, the host cell may be cultured for 1 hour to 72 hours at 18° C. to 40° C.

As the host cell culture medium, a medium known in the art may be used, and for example, a Luria-Bertani (LB) medium may be used, but it is not limited thereto.

When the host cell expresses a recombinant target protein by introducing the recombinant vector, the culture medium may further include an antibiotic for screening transformed microorganisms.

If necessary, the culture medium may further include isopropyl-1-thio-β-D-galactopyranoside (IPTG) for promoting expression of the recombinant target protein.

In the above-described method, the recombinant fibroblast growth factor 19 may be obtained by separating it from the culture of the host cell.

The culture may be a host cell or a culture medium thereof.

The host cell may be disrupted for easier separation of the recombinant fibroblast growth factor 19.

The host cell may be physically disrupted by ultrasonic irradiation, etc., or chemically destroyed by a surfactant, etc., but it is not limited thereto.

The culture medium may be a medium containing the host cell, or a medium from which the host cell is separated.

In addition, the production method of the present invention may further include the step of separating and purifying the recombinant fibroblast growth factor 19. The above step may be performed in connection with a conventional process in the art performed to use the produced protein for an intended use.

For a specific example, the above step may be performed by passing the culture through a column of anion exchange chromatography or heparin-affinity chromatography. When performing the anion exchange chromatography and heparin-affinity chromatography together, the anion exchange chromatography may be performed first.

The recombinant fibroblast growth factor 19 prepared according to the above-described method may have a disulfide bond well formed by DsbC expressed in the cytoplasm, such that soluble expression may be enhanced.

The recombinant fibroblast growth factor 19 may have an enhanced ability to activate a Ras-Raf-Erk1/2 MARK signaling pathway.

The present invention provides a pharmaceutical composition for treatment of diabetes or cancer comprising the recombinant fibroblast growth factor 19.

The pharmaceutical composition of the present invention may further contain one or more pharmaceutically acceptable carriers, excipients or diluents. As used herein, the term "pharmaceutically acceptable" refers to a composition that, when physiologically administering to a human, commonly does not cause an allergic reaction or a reaction similar thereto.

The composition may be delivered by a manner such as oral administration, parenteral administration, topical administration, or modified release, but it is not particularly limited thereto, and any manner may be selected so long as it can effectively deliver the composition of the present invention to a target site for promoting stem cell engraftment.

The composition of the present invention may be delivered by a transdermal absorption manner and specifically, may be delivered to the target site for promoting stem cell engraftment through a transdermal absorption pathway by manners such as attachment of a cataplasma or patch, adhesion of a plaster, attachment of a microneedle patch, injection of transdermal injections, applying an emulsion or dispersant including ointment or cream to the skin, and spraying a spray (including aerosol form), for example, but it is not particularly limited thereto. In this case, the composition of the present invention can be delivered more directly to the target site, such that it is possible to efficiently deliver by preventing denaturation in the delivery process, and may be relatively excellent in a delivery speed comparted to other methods.

In the oral administration, the composition of the present invention may be provided in a solid, semi-solid or liquid dosage form for oral administration. The oral administration also includes buccal and sublingual administrations. Suitable oral dosage forms may include tablets, fast melts (rapid dissolving tablets), chewable tablets, capsules, pills, strips, troches, lozenges, pastilles, cachets, pellets, medicinal chewing gum, bulk powders, effervescent or non-effervescent powders or granules, oral mist, solutions, emulsions, suspensions, wafers, sprinkles, elixirs and syrups, but it is not limited thereto. In addition to the active ingredient(s), the composition of the present invention includes binders, fillers, diluents, disintegrants, wetting agents, lubricants, glidants, coloring agents, dye-transfer inhibitors, sweeteners, fragrances, emulsifiers, suspending agents and dispersants, preservatives, solvents, oleaginous liquids, organic acids and carbon dioxide sources, but it is not limited thereto, and may include one or more excipients.

Suitable dosages of the composition vary by factors such as a formulation method, administration manner, age, body weight, sex of a patient, severity of disease symptoms, administration time, administration route, and response sensitization. Usually, skilled doctors may easily determine and prescribe effective dosages for treatment.

The present invention provides a composition for skin regeneration, revascularization, or antiobesity including the recombinant fibroblast growth factor 19.

The composition of the present invention may be used not only as a pharmaceutical composition as described above, but also in any formulation conventionally produced in the art. For example, the composition may be formulated as a solution, suspension, emulsion, paste, gel, cream, lotion, powder, soap, surfactant-containing cleanser, oil, powder foundation, emulsion foundation, wax foundation, spray, and the like, but it is not limited thereto.

When the formulation of the present invention is the paste, cream or gel, animal oil, vegetable oil, wax, paraffin, starch, tragacanth, cellulose derivative, polyethylene glycol, silicone, bentonite, silica, talc, zinc oxide, or the like may be used as a carrier component.

When the formulation of the present invention is the powder or spray, lactose, talc, silica, aluminum hydroxide, calcium silicate or polyamide powders may be used as the carrier component, and particularly, in the case of the spray, the composition may further include propellants such as chloro-fluorohydrocarbon, propane/butane or dimethyl ether.

When the formulation of the present invention is the solution or emulsion, a solvent, solubilizing agent or emulsifying agent may be used as the carrier component, and components such as water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or sorbitan fatty acid ester may be used.

When the formulation of the present invention is the suspension, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamido betaine, aliphatic alcohol, fatty acid glyceride, fatty acid diethanolamide, vegetable oil, lanolin derivative, ethoxylated glycerol fatty acid ester, or the like may be used as the carrier component.

The composition may be the pharmaceutical composition, and the pharmaceutical composition is as described above.

The composition may be a cosmetic composition.

The cosmetic composition may be formulated as a skin lotion, toner, beauty soap, body wash, serum, cleansing lotion, essence, nourishing cream, pack, massage cream, or the like, and in addition, may be formulated as a softening beauty wash, converging beauty wash, nourishing beauty wash, eye cream, eye essence, cleansing foam, cleansing water, powder, body lotion, body cream, body oil, body essence, makeup base, foundation, shampoo, rinse or the like, but it is not limited thereto.

When using as the cosmetic composition, substances may be further added thereto according to the formulation of a skin external application or cosmetic. For example, without limitation thereof, when the formulation is a paste, cream or gel, animal oil, vegetable oil, wax, paraffin, starch, tragacanth, cellulose derivative, polyethylene glycol, silicone, bentonite, silica, talc, zinc oxide or the like may be used. When the formulation is the powder or spray, lactose, talc, silica, aluminum hydroxide, calcium silicate, or polyamide powder may be used as the carrier component, and particularly, in the case of the spray, the composition may further include propellants such as chloro-fluorohydrocarbon, propane/butane or dimethyl ether. In addition, when the formulation is the solution or emulsion, a solvent, solubilizing agent or emulsifying agent may be used as the carrier component, and preferably, the formulation includes water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or sorbitan fatty acid ester, but it is not limited thereto. When the formulation is the suspension, liquid diluents such as water, ethanol or propylene glycol, suspending agents such as ethoxylated isostearyl alcohol, polyoxyethylene sorbitol esters and polyoxyethylene sorbitan esters, microcrystalline cellulose, aluminum metahydroxide, bentonite, agar, tragacanth, or the like may be used as the carrier component. When the formulation is the surfactant-containing cleanser, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamido betaine, aliphatic alcohol, fatty acid glyceride, fatty acid diethanolamide, vegetable oil, lanolin derivative, ethoxylated glycerol fatty acid ester, or the like may be used as the carrier component, but it is not limited thereto.

The composition may be a health functional food.

For example, the composition may be easily utilized as a main raw material or an auxiliary raw material of the food, a food additive, a functional food or beverage.

Foods to which the food composition can be added include, for example, various foods, beverages, gums, teas, vitamin complexes, and functional foods. Further, the foods include special nutritional foods (e.g., milk formulas, infant and baby foods, etc.), processed meat products, fish and meat products, bean curds, jellied foods, noodles (e.g. ramens, instant noodles, etc.), breads, health supplements, seasoned foods (e.g. soy sauce, miso, red pepper paste, mixed sauce, etc.), sauces, confectionery (e.g. snacks), candies, chocolates, gums, ice creams, dairy products (e.g. fermented milk, cheese, etc.), other processed foods, kimchi, pickled foods (various kimchis, pickles, etc.), beverages (e.g., fruit drinks, vegetable drinks, soy milks, fermented drinks, etc.), natural seasonings (e.g., ramen soup, etc.), but it is not limited thereto. The foods, beverages or food additives may be prepared by a conventional production method.

In addition, as used herein the term "functional food" or "health functional food" refers to a food group whose composition has added values so as to act and express the function of the food for a specific purpose by using physical, biochemical, or biotechnical methods, or foods designed and processed so as to sufficiently express body regulation functions in relation to regulation of immune system rhythms in the living body, disease prevention and recovery, etc., and specifically, may be the health functional food. The functional food may include food acceptable food supplement additives, and may further include suitable carriers, excipients, and diluents commonly used in the production of functional foods.

The type of the health supplement is not limited, but may be in a form of powders, granules, tablets, capsules or beverages.

Hereinafter, the present invention will be described in detail with reference to examples.

Figure 1:
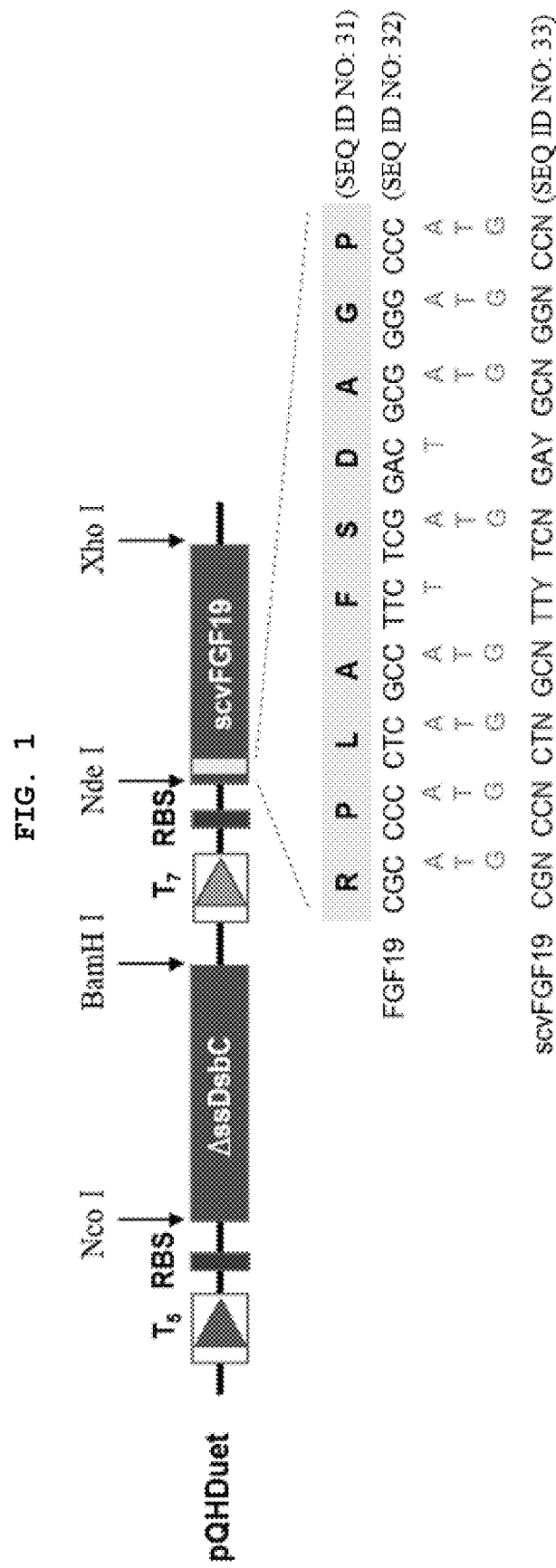
FIG. 1 is a schematic diagram of a recombinant duet vector prepared to express human fibroblast growth factor 19 in a soluble state.
Figure 2:
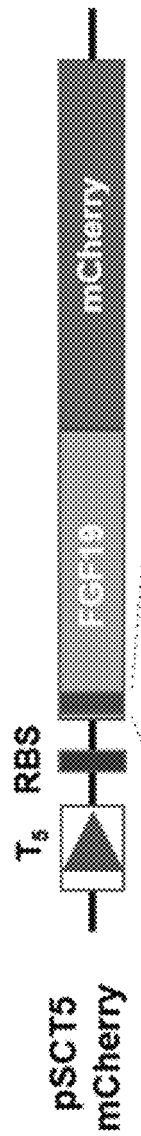
FIG. 2 is a schematic diagram of an expression vector to which synonymous codon substitution logic of the fibroblast growth factor 19 is applied.

Example 1: Screening of Human Fibroblast Growth Factor 19 (scvhFGF19) Having Increased Expression from Synonymous Codon Library In order to improve an expression pattern of wild type hFGF19 in which expression in *E. coli* is not observed, a synonymous codon library consisting of variants in which ten amino acid codons except for an initiation codon at the amino terminus of hFGF19 are substituted with synonymous codons was prepared. In order to facilitate the screening of variants having the improved expression from the synonymous codon library, as illustrated in FIG. 2, a plasmid designed so that the fluorescent protein mCherry is fused to the carboxyl terminus of hFGF19 was utilized. Information of the used primer is shown in Table 1 below.

TABLE 1

| Primer name | Sequence (5' → 3') | REase |
|---|---|---|
| pSCT5_FGF19-mC-fw | ATA<u>ACTAGT</u>ATGCGCCCCCTCGCCTTC (SEQ ID NO: 13) | SpeI |
| pSCT5_scvhFGF19-mC-fw | ATA<u>ACTAGT</u>ATGCGNCCNCTNGCNTTYTCNGAYGCN GGNCCNCACGTGCACT (SEQ ID NO: 14) | SpeI |
| pSCT5_FGF19-mC-rv | ATA<u>GGATCC</u>CTTCTCAAAGCTGGGACTCCTCAC (SEQ ID NO: 15) | BamHI |

TABLE 1-continued

| Primer name | Sequence (5' → 3') | REase |
|---|---|---|
| pSCT5_scvhFGF19-rv | ATAAAGCTTTTACTTCTCAAAGCTGGGACTCCTC (SEQ ID NO: 16) | HindIII |
| pSCT5_ΔssDsbC-fw | ATAACTAGTATGGATGACGCGGCAATTC (SEQ ID NO: 17) | SpeI |
| pSCT5_ΔssDsbC-rv | ATAGGATCCTTATTTACCGCTGGTCATTTTTTGGTG (SEQ ID NO: 18) | BamHI |
| pSCT5_FGF19/ΔssDsbC-fw | ATAGGATCCTAAATGGATGACGCGGCAATTCAAC (SEQ ID NO: 19) | BamHI |
| pSCT5_FGF19/ΔssDsbC-rv | ATAAAGCTTTTATTTACCGCTGGTCATTTTTTGGTGTTC (SEQ ID NO: 20) | HindIII |
| pSCT5_scvhFGF19-fw | ATACAATTTCACACAGAATTCATTAAAGAGGAGAAAGGATCCATGCG (SEQ ID NO: 21) | BamHI |
| pSCT5_scvhFGF19-rv | ATAAAGCTTTTACTTCTCAAAGCTGGGACTCCTC (SEQ ID NO: 22) | HindIII |
| pACYCDuet1_AssDsbC-fw | AGGAGATATACCATGGATGACGCGGCAATTCAACAACACG (SEQ ID NO: 23) | NcoI |
| pACYCDuet1_AssDsbC-rv | ATAGGATCCTTATTTACCGCTGGTCATTTTTTGGTGTTC (SEQ ID NO: 24) | BamHI |
| pACYCDuet1_scvhFGF19-fw | CAATTTCACACAGAATTCATTAAAGAGGAGAAACATATGCG (SEQ ID NO: 25) | NdeI |
| pACYCDuet1_scvhFGF19-rv | ATACTCGAGTTACTTCTCAAAGCTGGGACTCCTCACG (SEQ ID NO: 26) | XhoI |
| pQE80L V-fw | AGTTAATTTCTCCTCTTTAATGAATTCTGTGTG (SEQ ID NO: 27) | Infusion |
| pQE80L V-rv | CCGCCCTCTAGATTACGTGC (SEQ ID NO: 28) | Infusion |
| pQHDuet_InfuΔssDsbC-fw | GAGGAGAAATTAACTATGGATGACGCGGCAATTC (SEQ ID NO: 29) | Infusion |
| pQHDuet_InfuFGF19-rv | TAATCTAGAGGGCGGTTTTTAAGGCAGTTATTGGTGCCC (SEQ ID NO: 30) | Infusion |

The DNA fragment encoding 25 to 216 amino acid residues except for a signal sequence of human fibroblast growth factor 19 was amplified using a primer pair of pSCT5_scvFGF19-mC-fw and pSCT5_FGF19-mC-ry (Table 1) designed so that wobble bases are inserted into third base positions of the first ten amino acid codons except for the initiation codon, and pET24a_FGF19 provided from the Korea Institute of Ocean Science & Technology as a template. The PCR product was cleaved with SpeI and BamHI, cloned into a pSCT_mCherry vector cleaved with the same restriction enzyme, then transformed into E. coli XL1-Blue which is a typical cloning host and Origami 2 transformed so as to have an oxidative cytoplasmic environment, and then spread on a Luria-Bertani (LB) solid medium to which 100 μg/mL of ampicillin antibiotic was added to prepare a synonymous codon substitution library. Subsequently, after culturing at 37° C., colonies were selected in an order in which mCherry fluorescence fused to the carboxyl terminus of scvhFGF19 rapidly appeared to screen scvhFGF19 having increased expression.

In order to compare expression levels of wild type fibroblast growth factor (hFGF19) and the screened synonymous codon substitution variant fibroblast growth factor 19 (scvhFGF19), a single colony was inoculated in 3.5 mL of LB medium (10 g/L of NaCl, 10 g/L of tryptone, 5 g/L of yeast extract), cultured under conditions of 220 rpm and 37° C., and when absorbance ($OD_{600}$) of the culture liquid reached 2.0 to 2.5, 100 μl of the culture was reinoculated in 5 mL of a new LB medium having the same composition. By incubating under the same conditions, isopropyl-β-D-thiogalactopyranoside (IPTG) was added as an expression inducer so that the final concentration would be 0.2 mM when the absorbance ($OD_{600}$) reached 0.6 to 0.8. After the addition of IPTG, expression of fibroblast growth factor 19 was induced while further incubating for 3 hours at 250 rpm and 30° C.

After the culture was completed, the culture broth was corrected so that the absorbance ($OD_{600}$) would be 2.0, and centrifuged for 2 minutes under conditions of 13,200 rpm and 4° C. to obtain cells. After the obtained cells were suspended in 10 mM sodium phosphate buffer solution (pH 7.4), the cells were disrupted by sonicating twice with ultrasonic waves for 2 seconds. Immediately after disrupting the cells through ultrasonication, entire protein fractions were taken, followed by centrifugation for 20 minutes at 13,200 rpm and 4° C. to remove insoluble aggregates, then soluble fractions were obtained.

5× sample loading buffers (0.225 M Tris-HCl (pH 6.8), 50% glycerol, 5% SDS, 0.005 M bromophenol blue and 0.25 M dithiothreitol (DTT)) were added to the samples taken at each step in a ratio of 5:1, and heated for 15 minutes at 100° C. to induce denaturation of all proteins. Subsequently, as a result of electrophoresis using 12% SDS-PAGE, as illustrated in FIG. 3, when using *E. coli* XL1-Blue as a host for library preparation, expression of the wild type fibroblast growth factor 19 was not confirmed, whereas the screened synonymous codon substitution fibroblast growth factor 19 variants could be observed as an over-expressed state. However, it could be confirmed that most of the expressed proteins were in the form of insoluble aggregates. On the other hand, when using *E. coli* Origami 2 as the host, it could be confirmed that about 30% of the expressed scvhFGF19 was expressed in a soluble state.

Based on these results, for expression of scvhFGF19 from which mCherry fused as a reporter is removed from the variant screened in *E. coli* Origami 2 host, only scvhFGF19 was amplified from plasmid pSCT5_scvhFGF19-mCherry containing the synonymous codon substitution variants by using primers pSCT5_scvhFGF19-fw and pSCT5_scvhFGF19-rv as a template, then was cloned into pSCT5 vector cleaved with the same restriction enzyme by cleaving with BamHI and HindIII. After transforming pSCT5-scvhFGF19 expressing only the scvhFGF19 without mCherry fusion into Origami 2, the expression pattern was analyzed by inducing expression of scvhFGF19 in the same method as described above.

According to the analysis results, as can be confirmed in C of FIG. 3, the total expression level was maintained, but the soluble expression was still low. The above results show that, by merely using Origami 2 as a host cell, in which a transcription rate through synonymous codon substitution is controlled and a cytoplasmic environment is simply controlled for forming disulfide bonds, it is difficult to obtain hFGF19 in which two disulfide bonds are completely formed.

Example 2: Cytoplasmic Expression of Chaperone ΔssDsbC for Soluble Expression of scvhFGF19

As mentioned in Example 1, by knocking out trxB and gor encoding thioredoxin reductase and glutathione reductase, even in Origami 2 in which the disulfide bond by oxidation between two cysteine residues can be more easily formed, the soluble expression of hFGF19 was not simply achieved. As emphasized above, the results of Example 1 mean that it is difficult to correctly form two disulfide bonds of hFGF19 by merely changing the reducing environment for formation of disulfide bond.

Accordingly, the present inventors examined simultaneous expression of scvhFGF19 with the increased expression level in Origami 2 having an oxidative cytoplasm and ΔssDsbC from which a signal sequence is cleaved.

In order to express a disulfide bond isomerase (DsbC) protein together with the fibroblast growth factor 19 in the cytoplasm, the signal sequence was removed, and as plasmids shown first and second from the top in FIG. 4, a recombinant expression vector was prepared so that the scvhFGF19 and ΔssDsbC would be independently and simultaneously expressed by one promoter. A gene encoding the disulfide bond isomerase (DsbC) protein was obtained by performing PCR using genomic DNA of *E. coli* XL1-Blue as a template, and pSCT5_ΔssDsbC-fw and pSCT5_ΔssDsbC-rv primers shown in Table 1. The ΔssDsbC gene obtained through PCR was cleaved with a restriction enzyme SpeI and BamHI, and then inserted into pSCT5 mCherry empty vector cleaved with the same restriction enzyme to prepare a pSCT5_ΔssDsbC vector. Subsequently, PCR was performed using pSCT5_scvhFGF19 as a template, and pSCT5_scvFGF19-fw and pSCT5_scvFGF19-ry primers, and subjected to restriction enzyme treatment with BamHI and HindIII, then inserted into the prepared pSCT5_ΔssDsbC vector to produce pSCT5_ΔssDsbC/scvhFGF19 expression vector (plasmid shown first from the top in FIG. 4).

In addition, ΔssDsbC product amplified using pSCT5_FGF19/ΔssDsbC-fw and pSCT5_FGF19/ΔssDsbC-rv primers was subjected to restriction enzyme treatment with BamHI and HindIII, then inserted into a pSCT5_scvhFGF19 vector cleaved with the same restriction enzyme to produce pSCT5_scvhFGF19/ΔssDsbC vector (plasmid shown second from the top in FIG. 4).

In order to confirm the effect of simultaneous expression of ΔssDsbC on the expression pattern of scvhFGF19, the prepared recombinant expression vectors pSCT5_ΔssDsbC/scvFGF19 and pSCT5_scvFGF19/ΔssDsbC were introduced into *E. coli* host XL1-Blue, then the expression pattern of scvhFGF19 was analyzed using the method of Example 1. As a result, as illustrated in FIG. 5, it could be confirmed that scvhFGF19, which was mostly expressed in an insoluble state in *E. coli* XL1-Blue was expressed in a soluble state due to the simultaneous expression of ΔssDsbC. In addition, given that the expression level may be different according to the cloning position of ΔssDsbC, that is, according to the relative position of the promoter and two genes since the ΔssDsbC and scvhFGF19 are expressed together in a form of polycistronic mRNA, it can be seen that an expression ratio of the two genes affects the expression level and stability of scvhFGF19 in the cell.

Between the recombinant expression vectors pSCT5_ΔssDsbC/scvhFGF19 and pSCT5_scvhFGF19/ΔssDsbC, the former vector having a high expression level of scvhFGF19 was introduced into *E. coli* Origami 2 having a reducing cytoplasmic environment in which the disulfide bond is easily formed to analyze the expression pattern of scvhFGF19. As expected by the present inventors, it could be confirmed that the expression of scvhFGF19 was increased by about 2.5 times or more in Origami 2 as compared to the case of using *E. coli* XL1-Blue as a host, and more than 90% of the expressed scvhFGF19 was observed in the soluble fraction.

Example 3: Expression Control of ΔssDsbC for Increasing Soluble Expression of Synonymous Codon Substitution Variant Fibroblast Growth Factor 19 (scvhFGF19)

In Example 2, it was confirmed that the simultaneous expression of chaperone ΔssDsbC positively affects the solubility and stability of scvhFGF19. Based on these results, expression vectors having a dual expression system, in which the expressions of two genes are independently controlled by separate promoters, were produced in order to control the expression ratios of the two proteins.

(1) Confirmation of Expression of Synonymous Codon Substitution Variant Fibroblast Growth Factor 19 Using pACYCDuet Vector Controlled by Two Identical Promoters To produce vectors for independent simultaneous expression of ΔssDsbC and scvhFGF19, PCR was performed using pACYCDuet1_ΔssDsbC-fw and pACYCDuet1_ΔssDsbC-rv primers shown in Table 1 and the prepared pSCT5_ΔssDsbC/scvhFGF19 as a template, and the obtained product was inserted between NcoI and BamHI restriction enzyme recognition sequences present in the first multiple cloning site of pACYCDuet1 vector to produce a pACYCDuet1_ΔssDsbC vector. Then, the product, in which PCR was performed using pACYCDuet1 scvFGF19-fw and pACYCDuet1 scvFGF19-ry primers and pSCT5_ΔssDsbC/scvhFGF19 as a template, was inserted into NdeI and XhoI restriction enzyme recognition sequences within the second multi-cloning site of pACYCDuet1_ΔssDsbC vector to produce recombinant expression vector pACYCDuet1_ΔssDsbC/scvhFGF19 (plasmid shown third from the top in FIG. 4).

The constructed recombinant expression vector pACYCDuet1_ΔssDsbC/scvhFGF19 has the recognition sequence for T7 RNA polymerase, and thus transcriptions of each protein are controlled by two identical T7 promoters, and was transformed in *E. coli* host Origami (DE3) improved so as to have an oxidative environment. A single colony was inoculated in 3.5 mL of LB medium containing 25 μg/mL of chloramphenicol antibiotic, and cultured for 5 to 6 hours at 220 rpm and 37° C. Subsequently, 100 μl of the entire culture liquid was passaged in 5 mL of a fresh LB medium to which chloramphenicol was added, and then, when the absorbance ($OD_{600}$) of the culture liquid reached 0.6 to 0.8, IPTG was added so that the final concentration would be 0.2 mM, while culturing at 220 rpm and 37° C. After the addition, expression of human fibroblast growth factor 19 was induced for 3 hours at 250 rpm and 30° C. After the culture was completed, 5 mL of the culture liquid was centrifuged for 2 minutes at 13,200 rpm and 4° C. to obtain cells. After the obtained cells were suspended in 10 mM sodium phosphate buffer solution (pH 7.4), the cells were disrupted by sonicating twice with ultrasonic waves for 2 seconds. Immediately after disrupting the cells through ultrasonication, entire protein fractions were taken, followed by centrifugation for 20 minutes at 13,200 rpm and 4° C. to remove insoluble aggregates, then soluble fractions were obtained.

5× sample loading buffers (0.225 M Tris-HCl (pH 6.8), 50% glycerol, 5% SDS, 0.005 M bromophenol blue and 0.25 M dithiothreitol (DTT)) were added to the samples taken at each step in a ratio of 4:1, and heated for 15 minutes at 100° C. to induce denaturation of all proteins. Subsequently, electrophoresis and western blotting analysis were performed using 12% SDS-PAGE. As illustrated in FIG. 6, it can be confirmed that the expression of scvhFGF19 is increased as compared to the case in which expression is induced in a form of polycistronic mRNA expressing two genes in one promoter. However, during performing a repeated culture experiment for purification of scvhFGF19 using a transformant in which the pACYCDuet1_ΔssDsbC/scvhFGF19 is introduced, it was observed that the expression level and expression pattern of the fibroblast growth factor 19 were not evenly maintained. As one cause of these results, it can be considered that it is difficult to completely exclude a stochastic effect that can occur because one type of T7 RNA polymerase is bound to two T7 promoters which control the transcription of two genes (ΔssDsbC and scvhFGF19), respectively. Thereby, it is estimated that a difference in the expression ratio of the two genes occurring in each culture affects the soluble expression level of scvhFGF19. From the above results, it was determined that the transcription of the two genes is respectively controlled by different promoters, since it is difficult to secure reproducibility for soluble expression of the fibroblast growth factor 19 under the control of the same T7 promoter, also used for ΔssDsbC, of recombinant expression vector pACYCDuet1_ΔssDsbC/scvhFGF19, such that a new recombinant expression vector was produced.

(2) Confirmation of Expression of Synonymous Codon Substitution Variant Fibroblast Growth Factor 19 Using pQHDuet Vector Controlled by Two Different Promoters In order to solve the low reproducibility of the expression level and expression pattern of the synonymous codon substitution variant fibroblast growth factor 19 cloned into the pACYCDuet1 vector described in the above (1) item, the recombinant expression vector was improved so that two genes could be independently expressed.

To this end, pQE80L was used as a vector scaffold, and after removing a chloramphenicol resistance gene, the vector was designed so that transcription would be controlled by two different types of promoters, respectively. To produce a vector in which ΔssDsbC is expressed from T5 promoter and scvhFGF19 is expressed from T7 promoter, ΔssDsbC-T7 promoter-scvFGF19 region was amplified using pACYCDuet1_ΔssDsbC/scvhFGF19 as a template, and pQHDuet_InfuΔssDsbC-fw and pQHDuet_InfuFGF19-ry (Table 1), then cloned by using an infusion kit to produce recombinant expression vector pQHDuet_ΔssDsbC/scvhFGF19 (plasmid shown at a lower end in FIG. 4).

The constructed recombinant expression vector pQHDuet_ΔssDsbC/scvhFGF19 was introduced into *E. coli* host Origami (DE3), and the expression pattern was confirmed using the method performed in the above examples. As a result, as illustrated in FIG. 6, it could be confirmed that the soluble expression of scvhFGF19 produced from the recombinant expression vector pQHDuet_ΔssDsbC/scvhFGF19 was about 2 to 5 times higher than pSCT5_ΔssDsbC/scvhFGF19 and pACYCDuet1_ΔssDsbC/scvhFGF19, which are previously constructed recombinant expression vectors, and a deviation between the experiments is little.

Example 4: Purification of Synonymous Codon Substitution Variant Fibroblast Growth Factor 19 (scvFGF19)

Absolute purification of fibroblast growth factor 19 protein was performed in two steps by ion exchange chromatography using a Q-Sepharose high performance column (GE Healthcare) and heparin-affinity chromatography using a HiTrap heparin HP column.

The cells cultured in above Example 3-(2) were harvested, followed by centrifugation for 5 minutes at 6000 rpm and 4° C., and then freezing and thawing were repeated twice before ultrasonication for disrupting the obtained cells. Then, after suspension with 50 mL of 20 mM sodium phosphate buffer (pH 7.3) which is a mobile phase for application to anion exchange chromatography, ultrasonication for 2 seconds and stopping for 8 seconds were repeated for 4 minutes and 30 seconds to disrupt the cells. The cell lysate was centrifuged for 1 hour at 10,000 rpm and 4° C. to prepare a supernatant from which insoluble aggregates were removed. The supernatant containing scvhFGF19 was loaded at a flow rate of 1 mL/min into a Q-Sepharose high performance column (GE Healthcare) equilibrated with an elution buffer solution (20 mM sodium phosphate, pH 7.3). After the loading of the supernatant into the ion exchange resin column was completed, the supernatant was sufficiently washed with a binding buffer solution. Thereafter, a concentration gradient was induced so as to increase to 0 to 1 M NaCl for 150 ml (corresponding to 30 times the column volume) using an elution buffer solution (20 mM sodium phosphate, 1M NaCl, pH 7.3) to elute scvhFGF19, and fractions were obtained by 5 ml. When analyzing the fractions having absorbance at a wavelength of 280 nm among the obtained fractions by SDS-PAGE, as shown in FIG. 7, it could be observed that DsbC and scvhFGF19 were eluted between about 180 to 200 mM NaCl concentrations.

Subsequently, fractions containing only human fibroblast growth factor 19 were collected and sufficiently diluted with a binding buffer solution (20 mM sodium phosphate, pH 6.5), and then loaded at 0.5 mL/min on a heparin resin column equilibrated with the binding buffer solution. After the loading was completed, a concentration gradient was induced so as to reach 0.1 to 2 M NaCl for 40 ml using an elution buffer solution (20 mM sodium phosphate, 2 M NaCl, pH 6.5) to elute scvhFGF19. As a result, it was confirmed that scvhFGF19 was eluted around 500 mM NaCl similar to the previous reports (FIG. 7).

Example 5: Quantification of Purified Synonymous Codon Substitution Variant Fibroblast Growth Factor 19 (scvFGF19) Protein Purity of the protein of the purified synonymous codon substitution variant fibroblast growth factor 19 (scvhFGF19) was evaluated by SDS-PAGE analysis and western blotting analysis. In addition, the total protein concentration was measured as follows in a Bradford method using bovine serum albumin (BSA) as a standard protein sample. 5 μl of the purified protein diluted about 10-fold and 150 μl of Bradford reagent were mixed in a 96 well plate, followed by reacting for 5 minutes at room temperature, and then the concentration of the purified protein was measured at a wavelength of 595 nm using a spectrophotometer.

A purification yield of fibroblast growth factor 19 expressed using the recombinant expression vector pSCT5_ΔssDsbC/scvhFGF19 described in Example 2 was about 2 mg based on 1 L of a flask cell culture liquid, which is an increase of about 4 times compared to the previously reported yield (0.5 mg/L).

A purification yield of fibroblast growth factor 19 expressed using the recombinant expression vector pQHDuet_ΔssDsbC/scvhFGF19 described in above Example 3-(2) was about 5 mg based on 1 L of the flask cell culture liquid, which is an increase of about 10 times compared to the previously reported yield (0.5 mg/L).

Example 6: Functional Evaluation of Purified Synonymous Codon Substitution Variant Fibroblast Growth Factor 19 (scvFGF19)

Like human fibroblast growth factor 19 (hFGF19), a growth factor that triggers responses such as proliferation, differentiation and survival of a cell activates an extracellular signal regulated kinase (ERK) pathway in a vertebrate cell. Specifically, signaling between human FGF19 and fibroblast growth factor receptor 4 (FGFR4) activates a Ras-Raf-Erk1/2 MARK pathway. In other existing studies, a method, in which functional analysis for recombinant hFGF19 is confirmed through whether there is phosphorylation of a specific enzyme on the pathway in a human hepatocellular carcinoma cell (HepG2 cell) line, is used.

Therefore, the following experiment was performed in order to evaluate whether the synonymous codon substitution variant human fibroblast growth factor 19 (scvhFGF19) obtained by the two-step chromatography purification system of the present invention activates the Ras-Raf-Erk1/2 MARK signaling pathway.

First, the human hepatocellular carcinoma cell (HepG2 cell) line was cultured in a DMEM medium containing 10% fetal bovine serum (FBS), 100 U/mL penicillin and 100 μg/mL streptomycin. Then, before treating scvhFGF19, the cells were further cultured in the DMEM medium without FBS for 24 hours.

To evaluate the activity of the purified scvFGF19, an endotoxin was removed using an endotoxin removal spin column (Thermo Fisher Scientific), and then the protein was requantified with Bradford reagent. Subsequently, HepG2 cells were treated with 5 μg/mL of purified scvhFGF19 for 15 minutes, 30 minutes, 50 minutes, 90 minutes, and 120 minutes, respectively, and then the cells were lysed by treating a buffer (25 mM Tris-HCl pH 7.5, 150 mM NaCl, 1 mM EDTA, 1% NP-40) containing a protease inhibitor cocktail and a phosphatase inhibitor cocktail. From the lysate, activity was analyzed by performing immunoblotting using antibodies against Erk1/2 (Cell Signaling Technology), phosphorylated Erk1/2 (Cell Signaling Technology) and α-tubulin (Sigma-Aldrich).

A of FIG. 8 illustrates a degree of phosphorylation of Erk1/2 by scvhFGF19 when the treatment concentration of the purified scvhFGF19 is fixed at 5 μg/mL, and the treatment times are differently set to 15 minutes, 30 minutes, 60 minutes, 90 minutes, and 120 minutes. As can be seen in A of FIG. 8, the purified scvhFGF19 induced strong phosphorylation of Erk1/2 even a short-term treatment for 15 minutes, and the phosphorylated Erk1/2 decreased as the time after the treatment increased.

Meanwhile, the activity of the purified scvhFGF19 of the present invention was compared using recombinant FGF19 commercially available from ProSpec-Tany TechnoGene Ltd. as a positive control. B of FIG. 8 illustrates the degree of phosphorylation of Erk1/2 by scvhFGF19 when the treatment concentrations of the purified scvhFGF19 are differently set to 0.005 ng/mL, 0.05 ng/mL, 0.5 ng/mL, 5 ng/mL, 50 ng/mL, and 500 ng/mL, and the treatment time is set to be the same as each other. As can be seen in B of FIG. 8, it illustrates that phosphorylation of Erk1/2 by the purified scvhFGF19 was increased depending on the concentration of the treated scvhFGF19, and even when comparing to the case of the positive control treated with the same concentration, the phosphorylation degree of Erk1/2 by scvhFGF19 of the present invention is higher than that of Erk1/2 by the positive control.

These results exhibit that the recombinant expression vector for overexpressing the fibroblast growth factor 19 in a soluble state, and the scvhFGF19, which is produced and purified by using the FGF19 production method using the same and the efficient purification method, have Erk1/2 phosphorylation activity which is equivalent to or higher than the commercially available recombinant FGF19.

Although some embodiments of the present invention have been illustrated and described, those skilled in the art to which the present invention pertains will appreciate that various modifications are possible without departing from the principle or spirit of the present invention. The scope of the present invention will be defined by the appended claims and their equivalents.

A sequence listing electronically submitted with the present application on Aug. 19, 2020 as an ASCII text file named 20200819_LC0182014_TU_SEQ.txt, created on Aug. 18, 2020 and having a size of 52,275 bytes, is incorporated herein by reference in its entirety.

What is claimed is:

1. A recombinant vector for inducing soluble expression of fibroblast growth factor 19 (FGF19), the recombinant vector comprising:
   a first polynucleotide which encodes the fibroblast growth factor 19 (FGF19); and
   a second polynucleotide which encodes disulfide bond isomerase (DsbC),
   wherein the first polynucleotide consists of the sequence of SEQ ID NO: 3;
   wherein the second polynucleotide does not comprise a signal sequence;
   wherein the first polynucleotide and the second polynucleotide are operably linked to different promoters, respectively; and
   wherein the recombinant vector is designed to introduce into *Escherichia coli*.

2. The recombinant vector according to claim 1, wherein the second polynucleotide encodes a protein consisting of the amino acid sequence of SEQ ID NO: 2.

3. The recombinant vector according to claim 1,
   wherein the second polynucleotide consists of the sequence of SEQ ID NO: 4.

4. A method for producing recombinant fibroblast growth factor 19 comprising culturing *Escherichia coli* transformed with the recombinant vector according to claim 1.

* * * * *

SEQUENCE LISTING

<160> NUMBER OF SEQ ID NOS: 33

<210> SEQ ID NO 1
<211> LENGTH: 195
<212> TYPE: PRT
<213> ORGANISM: Homo sapiens

<400> SEQUENCE: 1

Met Arg Pro Leu Ala Phe Ser Asp Ala Gly Pro His Val His Tyr Gly
1               5                   10                  15

Trp Gly Asp Pro Ile Arg Leu Arg His Leu Tyr Thr Ser Gly Pro His
            20                  25                  30

Gly Leu Ser Ser Cys Phe Leu Arg Ile Arg Ala Asp Gly Val Val Asp
        35                  40                  45

Cys Ala Arg Gly Gln Ser Ala His Ser Leu Leu Glu Ile Lys Ala Val
    50                  55                  60

Ala Leu Arg Thr Val Ala Ile Lys Gly Val His Ser Val Arg Tyr Leu
65                  70                  75                  80

Cys Met Gly Ala Asp Gly Lys Met Gln Gly Leu Leu Gln Tyr Ser Glu
                85                  90                  95

Glu Asp Cys Ala Phe Glu Glu Glu Ile Arg Pro Asp Gly Tyr Asn Val
            100                 105                 110

Tyr Arg Ser Glu Lys His Arg Leu Pro Val Ser Leu Ser Ser Ala Lys
        115                 120                 125

Gln Arg Gln Leu Tyr Lys Asn Arg Gly Phe Leu Pro Leu Ser His Phe
    130                 135                 140

Leu Pro Met Leu Pro Met Val Pro Glu Glu Pro Glu Asp Leu Arg Gly
145                 150                 155                 160

His Leu Glu Ser Asp Met Phe Ser Ser Pro Leu Glu Thr Asp Ser Met
                165                 170                 175

Asp Pro Phe Gly Leu Val Thr Gly Leu Glu Ala Val Arg Ser Pro Ser
            180                 185                 190

Phe Glu Lys
        195

<210> SEQ ID NO 2
<211> LENGTH: 217
<212> TYPE: PRT
<213> ORGANISM: Artificial Sequence
<220> FEATURE:
<223> OTHER INFORMATION: DsbC

<400> SEQUENCE: 2

Met Asp Asp Ala Ala Ile Gln Gln Thr Leu Ala Lys Met Gly Ile Lys
1               5                   10                  15

Ser Ser Asp Ile Gln Pro Ala Pro Val Ala Gly Met Lys Thr Val Leu
            20                  25                  30

Thr Asn Ser Gly Val Leu Tyr Ile Thr Asp Asp Gly Lys His Ile Ile
        35                  40                  45

Gln Gly Pro Met Tyr Asp Val Ser Gly Thr Ala Pro Val Asn Val Thr
    50                  55                  60

Asn Lys Met Leu Leu Lys Gln Leu Asn Ala Leu Glu Lys Glu Met Ile
65                  70                  75                  80

Val Tyr Lys Ala Pro Gln Glu Lys His Val Ile Thr Val Phe Thr Asp
                85                  90                  95

Ile Thr Cys Gly Tyr Cys His Lys Leu His Glu Gln Met Ala Asp Tyr
            100                 105                 110

Asn Ala Leu Gly Ile Thr Val Arg Tyr Leu Ala Phe Pro Arg Gln Gly
        115                 120                 125

Leu Asp Ser Asp Ala Glu Lys Glu Met Lys Ala Ile Trp Cys Ala Lys
    130                 135                 140

Asp Lys Asn Lys Ala Phe Asp Asp Val Met Ala Gly Lys Ser Val Ala
145                 150                 155                 160

Pro Ala Ser Cys Asp Val Asp Ile Ala Asp His Tyr Ala Leu Gly Val
                165                 170                 175

Gln Leu Gly Val Ser Gly Thr Pro Ala Val Val Leu Ser Asn Gly Thr
            180                 185                 190

Leu Val Pro Gly Tyr Gln Pro Pro Lys Glu Met Lys Glu Phe Leu Asp
        195                 200                 205

Glu His Gln Lys Met Thr Ser Gly Lys
    210                 215

<210> SEQ ID NO 3
<211> LENGTH: 588
<212> TYPE: DNA
<213> ORGANISM: Artificial Sequence
<220> FEATURE:
<223> OTHER INFORMATION: scvhFGF19

<400> SEQUENCE: 3

| | | | | | |
|---|---|---|---|---|---|
| atgcgacctc | tagccttttc | cgatgcggga | cctcacgtgc | actacggctg | gggcgacccc | 60 |
| atccgcctgc | ggcacctgta | cacctccggc | ccccacgggc | tctccagctg | cttcctgcgc | 120 |
| atccgtgccg | acggcgtcgt | ggactgcgcg | cggggccaga | gcgcgcacag | tttgctggag | 180 |
| atcaaggcag | tcgctctgcg | gaccgtggcc | atcaagggcg | tgcacagcgt | cggtaccctc | 240 |
| tgcatgggcg | ccgacggcaa | gatgcagggg | ctgcttcagt | actcggagga | agactgtgct | 300 |
| ttcgaggagg | agatccgccc | agatggctac | aatgtgtacc | gatccgagaa | gcaccgcctc | 360 |
| ccggtctccc | tgagcagtgc | caaacagcgg | cagctgtaca | agaacagagg | ctttcttcca | 420 |
| ctctctcatt | tcctgcccat | gctgcccatg | gtcccagagg | agcctgagga | cctcaggggc | 480 |
| cacttggaat | ctgacatgtt | ctcttcgccc | ctggagaccg | acagcatgga | cccatttggg | 540 |
| cttgtcaccg | gactggaggc | cgtgaggagt | cccagctttg | agaagtaa | | 588 |

<210> SEQ ID NO 4
<211> LENGTH: 654
<212> TYPE: DNA
<213> ORGANISM: Artificial Sequence
<220> FEATURE:
<223> OTHER INFORMATION: DsbC

<400> SEQUENCE: 4

| | | | | | |
|---|---|---|---|---|---|
| atggatgacg | cggcaattca | acaaacgtta | gccaaaatgg | gcatcaaaag | cagcgatatt | 60 |
| cagcccgcgc | tgtagctgg | catgaagaca | gttctgacta | acagcggcgt | gttgtacatc | 120 |
| accgatgatg | gtaaacatat | cattcagggg | ccaatgtatg | acgttagtgg | cacggctccg | 180 |
| gtcaatgtca | ccaataagat | gctgttaaag | cagttgaatg | cgcttgaaaa | agagatgatc | 240 |
| gtttataaag | cgccgcagga | aaaacacgtc | atcaccgtgt | ttactgatat | tacctgtggt | 300 |
| tactgccaca | aactgcatga | gcaaatggca | gactacaacg | cgctggggat | caccgtgcgt | 360 |
| tatcttgctt | tcccgcgcca | ggggctggac | agcgatgcag | agaaagaaat | gaaagctatc | 420 |
| tggtgtgcga | agataaaaaa | caaagcgttt | gatgatgtga | tggcaggtaa | aagcgtcgca | 480 |
| ccagccagtt | gcgacgtgga | tattgccgac | cattacgcac | ttggcgtcca | gcttggcgtt | 540 |

```
agcggtactc cggcagttgt gctgagcaat ggcacacttg ttccgggtta ccagccgccg    600
aaagagatga aagaattcct cgacgaacac caaaaaatga ccagcggtaa ataa         654
```

<210> SEQ ID NO 5
<211> LENGTH: 588
<212> TYPE: DNA
<213> ORGANISM: Homo sapiens

<400> SEQUENCE: 5

```
atgcgccccc tcgccttctc ggacgcgggg ccccacgtgc actacggctg gggcgacccc    60
atccgcctgc ggcacctgta cacctccggc ccccacgggc tctccagctg cttcctgcgc   120
atccgtgccg acggcgtcgt ggactgcgcg cggggccaga gcgcgcacag tttgctggag   180
atcaaggcag tcgctctgcg gaccgtggcc atcaagggcg tgcacagcgt gcggtacctc   240
tgcatgggcg ccgacggcaa gatgcagggg ctgcttcagt actcggagga agactgtgct   300
ttcgaggagg agatccgccc agatggctac aatgtgtacc gatccgagaa gcaccgcctc   360
ccggtctccc tgagcagtgc caaacagcgg cagctgtaca gaacagagg ctttcttcca    420 ctctctcatt tcctgcccat gctgcccatg gtcccagagg agcctgagga cctcaggggc   480
cacttggaat ctgacatgtt ctcttcgccc ctggagaccg acagcatgga cccatttggg   540
cttgtcaccg gactggaggc cgtgaggagt cccagctttg agaagtaa                 588
```

<210> SEQ ID NO 6
<211> LENGTH: 435
<212> TYPE: PRT
<213> ORGANISM: Artificial Sequence
<220> FEATURE:
<223> OTHER INFORMATION: scvhFGF19-mCherry

<400> SEQUENCE: 6

```
Met Arg Pro Leu Ala Phe Ser Asp Ala Gly Pro His Val His Tyr Gly
1               5                   10                  15

Trp Gly Asp Pro Ile Arg Leu Arg His Leu Tyr Thr Ser Gly Pro His
            20                  25                  30

Gly Leu Ser Ser Cys Phe Leu Arg Ile Arg Ala Asp Gly Val Val Asp
        35                  40                  45

Cys Ala Arg Gly Gln Ser Ala His Ser Leu Leu Glu Ile Lys Ala Val
    50                  55                  60

Ala Leu Arg Thr Val Ala Ile Lys Gly Val His Ser Val Arg Tyr Leu
65                  70                  75                  80

Cys Met Gly Ala Asp Gly Lys Met Gln Gly Leu Leu Gln Tyr Ser Glu
                85                  90                  95

Glu Asp Cys Ala Phe Glu Glu Glu Ile Arg Pro Asp Gly Tyr Asn Val
            100                 105                 110

Tyr Arg Ser Glu Lys His Arg Leu Pro Val Ser Leu Ser Ser Ala Lys
        115                 120                 125

Gln Arg Gln Leu Tyr Lys Asn Arg Gly Phe Leu Pro Leu Ser His Phe
    130                 135                 140

Leu Pro Met Leu Pro Met Val Pro Glu Glu Pro Glu Asp Leu Arg Gly
145                 150                 155                 160

His Leu Glu Ser Asp Met Phe Ser Ser Pro Leu Glu Thr Asp Ser Met
                165                 170                 175

Asp Pro Phe Gly Leu Val Thr Gly Leu Glu Ala Val Arg Ser Pro Ser
            180                 185                 190
```

```
Phe Glu Lys Gly Ser Gly Thr Met Val Ser Lys Gly Glu Asp Asn
            195                 200                 205
Met Ala Ile Ile Lys Glu Phe Met Arg Phe Lys Val His Met Glu Gly
210                 215                 220
Ser Val Asn Gly His Glu Phe Glu Ile Glu Gly Glu Gly Glu Gly Arg
225                 230                 235                 240
Pro Tyr Glu Gly Thr Gln Thr Ala Lys Leu Lys Val Thr Lys Gly Gly
            245                 250                 255
Pro Leu Pro Phe Ala Trp Asp Ile Leu Ser Pro Gln Phe Met Tyr Gly
            260                 265                 270
Ser Lys Ala Tyr Val Lys His Pro Ala Asp Ile Pro Asp Tyr Leu Lys
            275                 280                 285
Leu Ser Phe Pro Glu Gly Phe Lys Trp Glu Arg Val Met Asn Phe Glu
            290                 295                 300
Asp Gly Gly Val Val Thr Val Thr Gln Asp Ser Ser Leu Gln Asp Gly
305                 310                 315                 320
Glu Phe Ile Tyr Lys Val Lys Leu Arg Gly Thr Asn Phe Pro Ser Asp
                325                 330                 335
Gly Pro Val Met Gln Lys Lys Thr Met Gly Trp Glu Ala Ser Ser Glu
            340                 345                 350
Arg Met Tyr Pro Glu Asp Gly Ala Leu Lys Gly Glu Ile Lys Gln Arg
            355                 360                 365
Leu Lys Leu Lys Asp Gly Gly His Tyr Asp Ala Glu Val Lys Thr Thr
            370                 375                 380
Tyr Lys Ala Lys Lys Pro Val Gln Leu Pro Gly Ala Tyr Asn Val Asn
385                 390                 395                 400
Ile Lys Leu Asp Ile Thr Ser His Asn Glu Asp Tyr Thr Ile Val Glu
                405                 410                 415
Gln Tyr Glu Arg Ala Glu Gly Arg His Ser Thr Gly Gly Met Asp Glu
            420                 425                 430
Leu Tyr Lys
        435

<210> SEQ ID NO 7
<211> LENGTH: 414
<212> TYPE: PRT
<213> ORGANISM: Artificial Sequence
<220> FEATURE:
<223> OTHER INFORMATION: DsbC-scvhFGF19

<400> SEQUENCE: 7

Met Asp Asp Ala Ala Ile Gln Gln Thr Leu Ala Lys Met Gly Ile Lys
1               5                   10                  15
Ser Ser Asp Ile Gln Pro Ala Pro Val Ala Gly Met Lys Thr Val Leu
            20                  25                  30
Thr Asn Ser Gly Val Leu Tyr Ile Thr Asp Asp Gly Lys His Ile Ile
            35                  40                  45
Gln Gly Pro Met Tyr Asp Val Ser Gly Thr Ala Pro Val Asn Val Thr
        50                  55                  60
Asn Lys Met Leu Leu Lys Gln Leu Asn Ala Leu Glu Lys Glu Met Ile
65                  70                  75                  80
Val Tyr Lys Ala Pro Gln Glu Lys His Val Ile Thr Val Phe Thr Asp
                85                  90                  95
Ile Thr Cys Gly Tyr Cys His Lys Leu His Glu Gln Met Ala Asp Tyr
            100                 105                 110
```

```
Asn Ala Leu Gly Ile Thr Val Arg Tyr Leu Ala Phe Pro Arg Gln Gly
            115                 120                 125

Leu Asp Ser Asp Ala Glu Lys Glu Met Lys Ala Ile Trp Cys Ala Lys
130                 135                 140

Asp Lys Asn Lys Ala Phe Asp Asp Val Met Ala Gly Lys Ser Val Ala
145                 150                 155                 160

Pro Ala Ser Cys Asp Val Asp Ile Ala Asp His Tyr Ala Leu Gly Val
                165                 170                 175

Gln Leu Gly Val Ser Gly Thr Pro Ala Val Val Leu Ser Asn Gly Thr
            180                 185                 190

Leu Val Pro Gly Tyr Gln Pro Pro Lys Glu Met Lys Glu Phe Leu Asp
        195                 200                 205

Glu His Gln Lys Met Thr Ser Gly Lys Gly Ser Met Arg Pro Leu Ala
    210                 215                 220

Phe Ser Asp Ala Gly Pro His Val His Tyr Gly Trp Gly Asp Pro Ile
225                 230                 235                 240

Arg Leu Arg His Leu Tyr Thr Ser Gly Pro His Gly Leu Ser Ser Cys
                245                 250                 255

Phe Leu Arg Ile Arg Ala Asp Gly Val Val Asp Cys Ala Arg Gly Gln
            260                 265                 270

Ser Ala His Ser Leu Leu Glu Ile Lys Ala Val Ala Leu Arg Thr Val
        275                 280                 285

Ala Ile Lys Gly Val His Ser Val Arg Tyr Leu Cys Met Gly Ala Asp
    290                 295                 300

Gly Lys Met Gln Gly Leu Leu Gln Tyr Ser Glu Glu Asp Cys Ala Phe
305                 310                 315                 320

Glu Glu Glu Ile Arg Pro Asp Gly Tyr Asn Val Tyr Arg Ser Glu Lys
                325                 330                 335

His Arg Leu Pro Val Ser Leu Ser Ser Ala Lys Gln Arg Gln Leu Tyr
            340                 345                 350

Lys Asn Arg Gly Phe Leu Pro Leu Ser His Phe Leu Pro Met Leu Pro
        355                 360                 365

Met Val Pro Glu Glu Pro Glu Asp Leu Arg Gly His Leu Glu Ser Asp
    370                 375                 380

Met Phe Ser Ser Pro Leu Glu Thr Asp Ser Met Asp Pro Phe Gly Leu
385                 390                 395                 400

Val Thr Gly Leu Glu Ala Val Arg Ser Pro Ser Phe Glu Lys
                405                 410

<210> SEQ ID NO 8
<211> LENGTH: 4697
<212> TYPE: DNA
<213> ORGANISM: Artificial Sequence
<220> FEATURE:
<223> OTHER INFORMATION: pSCT5_FGF19-mCherry

<400> SEQUENCE: 8
ctcgagaaat cataaaaaat ttatttgctt tgtgagcgga taacaattat aatagattca     60
attgtgagcg gataacaatt tcacacagaa ttcattaaag aggagaaaac tagtatgcgc    120
cccctcgcct tctcggacgc ggggccccac gtgcactacg gctggggcga ccccatccgc    180
ctgcggcacc tgtacacctc cggcccccac gggctctcca gctgcttcct gcgcatccgt    240
gccgacggcg tcgtggactg cgcgcggggc cagagcgcgc acagtttgct ggagatcaag    300
gcagtcgctc tgcggaccgt ggccatcaag ggcgtgcaca cgtgcggta cctctgcatg    360
```

```
ggcgccgacg gcaagatgca ggggctgctt cagtactcgg aggaagactg tgctttcgag    420
gaggagatcc gcccagatgg ctacaatgtg taccgatccg agaagcaccg cctcccggtc    480
tccctgagca gtgccaaaca gcggcagctg tacaagaaca gaggctttct tccactctct    540
catttcctgc ccatgctgcc catggtccca gaggagcctg aggacctcag ggccacttg     600 gaatctgaca tgttctcttc gccctggag accgacagca tggacccatt tgggcttgtc    660
accggactgg aggccgtgag gagtcccagc tttgagaagg gatccggtac catggtgagc    720
aagggcgagg aggataacat ggccatcatc aaggagttca tgcgcttcaa ggtgcacatg    780
gagggctccg tgaacggcca cgagttcgag atcgagggcg agggcgaggg ccgcccctac    840
gagggcaccc agaccgccaa gctgaaggtg accaagggtg gccccctgcc cttcgcctgg    900
gacatcctgt cccctcagtt catgtaccgg tccaaggcct acgtgaagca ccccgccgac    960
atccccgact acttgaagct gtccttcccc gagggcttca gtgggagcg cgtgatgaac    1020 ttcgaggacg gcggcgtggt gaccgtgacc caggactcct ccctgcagga cggcgagttc    1080
atctacaagg tgaagctgcg cggcaccaac ttcccctccg acggccccgt aatgcagaag    1140
aagaccatgg gctgggaggc ctcctccgag cggatgtacc ccgaggacgg cgccctgaag    1200
ggcgagatca gcagaggct gaagctgaag gacggcggcc actacgacgc tgaggtcaag    1260
accacctaca aggccaagaa gcccgtgcag ctgcccggcg cctacaacgt caacatcaag    1320
ttggacatca cctcccacaa cgaggactac accatcgtgg aacagtacga acgcgccgag    1380
ggccgccact ccaccggcgg catggacgag ctgtacaagt agaagcttaa ttagctgagc    1440
ttggactcct gttgatagat ccagtaatga cctcagaact ccatctggat ttgttcagaa    1500
cgctcggttg ccgccgggcg ttttttattg gtgagaatcc aagctagctt ggcgagattt    1560
tcaggagcta aggaagctaa aatggagaaa aaaatcactg gatataccac cgttgatata    1620
tcccaatggc atcgtaaaga acattttgag gcatttcagt cagttgctca atgtacctat    1680
aaccagaccg ttcagctgga tattacggcc ttttttaaaga ccgtaaagaa aaataagcac    1740 aagtttttatc cggcctttat tcacattctt gcccgcctga tgaatgctca tccggaattt    1800
cgtatggcaa tgaaagacgg tgagctggtg atatgggata gtgttcaccc ttgttacacc    1860
gttttccatg agcaaactga aacgttttca tcgctctgga gtgaatacca cgacgatttc    1920
cggcagtttc tacacatata ttcgcaagat gtggcgtgtt acggtgaaaa cctggcctat    1980
ttccctaaag ggtttattga gaatatgttt ttcgtctcag ccaatccctg ggtgagtttc    2040
accagttttg atttaaacgt ggccaatatg gacaacttct tcgcccccgt tttcaccatg    2100
ggcaaatatt atacgcaagg cgacaaggtg ctgatgccgc tggcgattca ggttcatcat    2160
gccgtttgtg atggcttcca tgtcggcaga atgcttaatg aattacaaca gtactgcgat    2220
gagtggcagg gcggggcgta atttttttaa ggcagttatt ggtgccctta aacgcctggg    2280
gtaatgactc tctagcttga ggcatcaaat aaaacgaaag gctcagtcga agactgggc    2340 ctttcgtttt atctgttgtt tgtcggtgaa cgctctcctg agtaggacaa atccgccctc    2400
tagagctgcc tcgcgcgttt cggtgatgac ggtgaaaacc tctgacacat gcagctcccg    2460
gagacggtca gcttgtctgt gtaagcggat gccgggagca gacaagcccg tcagggcgcg    2520
tcagcgggtg ttggcgggtg tcggggcgca gccatgaccc agtcacgtag cgatagcgga    2580
gtgtatactg gcttaactat gcggcatcag agcagattgt actgagagtg caccatatgc    2640
ggtgtgaaat accgcacaga tgcgtaagga gaaaataccg catcaggcgc tcttccgctt    2700
cctcgctcac tgactcgctg cgctcggtcg ttcggctgcg gcgagcggta tcagctcact    2760
```

```
caaaggcggt aatacggtta tccacagaat caggggataa cgcaggaaag aacatgtgag    2820
caaaaggcca gcaaaaggcc aggaaccgta aaaaggccgc gttgctggcg ttttttccata   2880 ggctccgccc ccctgacgag catcacaaaa atcgacgctc aagtcagagg tggcgaaacc   2940
cgacaggact ataaagatac caggcgtttc ccccctggaag ctccctcgtg cgctctcctg   3000
ttccgaccct gccgcttacc ggatacctgt ccgcctttct cccttcggga agcgtggcgc   3060
tttctcatag ctcacgctgt aggtatctca gttcggtgta ggtcgttcgc tccaagctgg   3120
gctgtgtgca cgaaccccccc gttcagcccg accgctgcgc cttatccggt aactatcgtc   3180
ttgagtccaa cccggtaaga cacgacttat cgccactggc agcagccact ggtaacagga   3240
ttagcagagc gaggtatgta ggcggtgcta cagagttctt gaagtggtgg cctaactacg   3300
gctacactag aaggacagta tttggtatct gcgctctgct gaagccagtt accttcggaa   3360
aaagagttgg tagctcttga tccggcaaac aaaccaccgc tggtagcggt ggtttttttg   3420
tttgcaagca gcagattacg cgcagaaaaa aaggatctca agaagatcct ttgatctttt   3480
ctacggggtc tgacgctcag tggaacgaaa actcacgtta agggattttg gtcatgagat   3540
tatcaaaaag gatcttcacc tagatccttt taaattaaaa atgaagtttt aaatcaatct   3600
aaagtatata tgagtaaact tggtctgaca gttaccaatg cttaatcagt gaggcaccta   3660
tctcagcgat ctgtctattt cgttcatcca tagttgcctg actccccgtc gtgtagataa   3720
ctacgatacg ggagggctta ccatctggcc ccagtgctgc aatgataccg cgagacccac   3780
gctcaccggc tccagattta tcagcaataa accagccagc cggaagggcc gagcgcagaa   3840
gtggtcctgc aactttatcc gcctccatcc agtctattaa ttgttgccgg gaagctagag   3900
taagtagttc gccagttaat agtttgcgca acgttgttgc cattgctaca ggcatcgtgg   3960
tgtcacgctc gtcgtttggt atggcttcat tcagctccgg ttcccaacga tcaaggcgag   4020
ttacatgatc ccccatgttg tgcaaaaaag cggttagctc cttcggtcct ccgatcgttg   4080
tcagaagtaa gttggccgca gtgttatcac tcatggttat ggcagcactg cataattctc   4140
ttactgtcat gccatccgta agatgctttt ctgtgactgg tgagtactca accaagtcat   4200
tctgagaata gtgtatgcgg cgaccgagtt gctcttgccc ggcgtcaata cgggataata   4260
ccgcgccaca tagcagaact ttaaaagtgc tcatcattgg aaaacgttct cggggcgaa    4320 aactctcaag gatcttaccg ctgttgagat ccagttcgat gtaacccact cgtgcaccca   4380
actgatcttc agcatctttt actttcacca gcgtttctgg gtgagcaaaa acaggaaggc   4440
aaaatgccgc aaaaaaggga ataagggcga cacggaaatg ttgaatactc atactcttcc   4500
tttttcaata ttattgaagc atttatcagg gttattgtct catgagcgga tacatatttg   4560
aatgtattta gaaaaataaa caaatagggg ttccgcgcac atttccccga aaagtgccac   4620
ctgacgtcta agaaaccatt attatcatga cattaaccta taaaaatagg cgtatcacga   4680
ggccctttcg tcttcac                                                  4697
```

<210> SEQ ID NO 9
<211> LENGTH: 4696
<212> TYPE: DNA
<213> ORGANISM: Artificial Sequence
<220> FEATURE:
<223> OTHER INFORMATION: pSCT5_scvhFGF19-mCherry

<400> SEQUENCE: 9

```
ctcgagaaat cataaaaaat ttatttgctt tgtgagcgga taacaattat aatagattca     60
```

-continued

```
attgtgagcg ataacaatt tcacacagaa ttcattaaag aggagaaaac tagtatgcga      120
cctctagcct tttccgatgc gggacctcac gtgcactacg gctggggcga ccccatccgc    180
ctgcggcacc tgtacacctc cggcccccac gggctctcca gctgcttcct gcgcatccgt    240
gccgacggcg tcgtggactg cgcgcggggc cagagcgcgc acagtttgct ggagatcaag    300
gcagtcgctc tgcggaccgt ggccatcaag ggcgtgcaca gcgtgcggta cctctgcatg    360
ggcgccgacg gcaagatgca ggggctgctt cagtactcgg aggaagactg tgctttcgag    420
gaggagatcc gcccagatgg ctacaatgtg taccgatccg agaagcaccg cctcccggtc    480
tccctgagca gtgccaaaca gcggcagctg tacaagaaca gaggctttct tccactctct    540
catttcctgc ccatgctgcc catggtccca gaggagcctg aggacctcag gggccacttg    600
gaatctgaca tgttctcttc gcccctggag accgacagca tggacccatt tgggcttgtc    660
accggactgg aggccgtgag gagtcccagc tttgagaagg atccggtacc atggtgagca    720
agggcgagga ggataacatg gccatcatca aggagttcat gcgcttcaag gtgcacatgg    780
agggctccgt gaacggccac gagttcgaga tcgagggcga gggcgagggc cgcccctacg    840
agggcaccca gaccgccaag ctgaaggtga ccaagggtgg ccccctgccc ttcgcctggg    900
acatcctgtc ccctcagttc atgtacggct ccaaggccta cgtgaagcac cccgccgaca    960
tccccgacta cttgaagctg tccttccccg agggcttcaa gtgggagcgc gtgatgaact   1020
tcgaggacgg cggcgtggtg accgtgaccc aggactcctc cctgcaggac ggcgagttca   1080
tctacaaggt gaagctgcgc ggcaccaact tcccctccga cggccccgta atgcagaaga   1140
agaccatggg ctgggaggcc tcctccgagc ggatgtaccc cgaggacggc gccctgaagg   1200
gcgagatcaa gcagaggctg aagctgaagg acggcggcca ctacgacgct gaggtcaaga   1260
ccacctacaa ggccaagaag cccgtgcagc tgcccggcgc ctacaacgtc aacatcaagt   1320
tggacatcac ctcccacaac gaggactaca ccatcgtgga acagtacgaa cgcgccgagg   1380
gccgccactc caccggcggc atggacgagc tgtacaagta gaagcttaat tagctgagct   1440
tggactcctg ttgatagatc cagtaatgac ctcagaactc catctggatt tgttcagaac   1500
gctcggttgc cgccgggcgt tttttattgg tgagaatcca agctagcttg gcgagatttt   1560
caggagctaa ggaagctaaa atggagaaaa aaatcactgg atataccacc gttgatatat   1620
cccaatggca tcgtaaagaa catttgaggg catttcagtc agttgctcaa tgtacctata   1680
accagaccgt tcagctggat attacggcct tttaaagac cgtaaagaaa ataagcaca    1740 agttttatcc ggcctttatt cacattcttg cccgcctgat gaatgctcat ccggaatttc   1800
gtatggcaat gaaagacggt gagctggtga tatgggatag tgttcaccct tgttacaccg   1860
ttttccatga gcaaactgaa acgttttcat cgctctggag tgaataccac gacgatttcc   1920
ggcagtttct acacatatat tcgcaagatg tggcgtgtta cggtgaaaac ctggcctatt   1980
tccctaaagg gtttattgag aatatgtttt tcgtctcagc caatccctgg gtgagtttca   2040
ccagttttga tttaaacgtg gccaatatgg acaacttctt cgccccgtt ttcaccatgg    2100 gcaaatatta tacgcaaggc gacaaggtgc tgatgccgct ggcgattcag gttcatcatg   2160
ccgtttgtga tggcttccat gtcggcagaa tgcttaatga attacaacag tactgcgatg   2220
agtggcaggg cggggcgtaa ttttttaag gcagttattg gtgcccttaa acgcctgggg    2280
taatgactct ctagcttgag gcatcaaata aaacgaaagg ctcagtcgaa agactgggcc   2340
tttcgtttta tctgttgttt gtcggtgaac gctctcctga gtaggacaaa tccgccctct   2400
agagctgcct cgcgcgtttc ggtgatgacg gtgaaaacct ctgacacatg cagctcccgg   2460
```

```
agacggtcac agcttgtctg taagcggatg ccgggagcag acaagcccgt cagggcgcgt    2520
cagcgggtgt tggcgggtgt cggggcgcag ccatgaccca gtcacgtagc gatagcggag    2580
tgtatactgg cttaactatg cggcatcaga gcagattgta ctgagagtgc accatatgcg    2640
gtgtgaaata ccgcacagat gcgtaaggag aaaataccgc atcaggcgct cttccgcttc    2700
ctcgctcact gactcgctgc gctcggtcgt tcggctgcgg cgagcggtat cagctcactc    2760
aaaggcggta atacggttat ccacagaatc aggggataac gcaggaaaga acatgtgagc    2820
aaaaggccag caaaaggcca ggaaccgtaa aaaggccgcg ttgctggcgt ttttccatag    2880
gctccgcccc cctgacgagc atcacaaaaa tcgacgctca agtcagaggt ggcgaaaccc    2940
gacaggacta taaagatacc aggcgtttcc ccctggaagc tccctcgtgc gctctcctgt    3000
tccgaccctg ccgcttaccg gatacctgtc cgcctttctc ccttcgggaa gcgtggcgct    3060
ttctcatagc tcacgctgta ggtatctcag ttcggtgtag gtcgttcgct ccaagctggg    3120
ctgtgtgcac gaaccccccg ttcagcccga ccgctgcgcc ttatccggta actatcgtct    3180
tgagtccaac ccggtaagac acgacttatc gccactggca gcagccactg gtaacaggat    3240
tagcagagcg aggtatgtag gcggtgctac agagttcttg aagtggtggc ctaactacgg    3300
ctacactaga aggacagtat ttggtatctg cgctctgctg aagccagtta ccttcggaaa    3360
aagagttggt agctcttgat ccggcaaaca aaccaccgct ggtagcggtg gttttttgt    3420 ttgcaagcag cagattacgc gcagaaaaaa aggatctcaa gaagatcctt tgatcttttc    3480
tacggggtct gacgctcagt ggaacgaaaa ctcacgttaa gggattttgg tcatgagatt    3540
atcaaaaagg atcttcacct agatcctttt aaattaaaaa tgaagtttta atcaatcta    3600 aagtatatat gagtaaactt ggtctgacag ttaccaatgc ttaatcagtg aggcaccta    3660 ctcagcgatc tgtctatttc gttcatccat agttgcctga ctccccgtcg tgtagataac    3720
tacgatacgg gagggcttac catctggccc cagtgctgca atgataccgc gagacccacg    3780
ctcaccggct ccagatttat cagcaataaa ccagccagcc ggaagggccg agcgcagaag    3840
tggtcctgca actttatccg cctccatcca gtctattaat tgttgccggg aagctagagt    3900
aagtagttcg ccagttaata gtttgcgcaa cgttgttgcc attgctacag gcatcgtggt    3960
gtcacgctcg tcgtttggta tggcttcatt cagctccggt tcccaacgat caaggcgagt    4020
tacatgatcc cccatgttgt gcaaaaaagc ggttagctcc ttcggtcctc cgatcgttgt    4080
cagaagtaag ttggccgcag tgttatcact catggttatg gcagcactgc ataattctct    4140
tactgtcatg ccatccgtaa gatgcttttc tgtgactggt gagtactcaa ccaagtcatt    4200
ctgagaatag tgtatgcggc gaccgagttg ctcttgcccg gcgtcaatac gggataatac    4260
cgcgccacat agcagaactt taaaagtgct catcattgga aaacgttctt cggggcgaaa    4320
actctcaagg atcttaccgc tgttgagatc cagttcgatg taacccactc gtgcacccaa    4380
ctgatcttca gcatctttta ctttcaccag cgtttctggg tgagcaaaaa caggaaggca    4440
aaatgccgca aaaaagggaa taagggcgac acggaaatgt tgaatactca tactcttcct    4500
ttttcaatat tattgaagca tttatcaggg ttattgtctc atgagcggat acatatttga    4560
atgtatttag aaaaataaac aaataggggt tccgcgcaca tttccccgaa aagtgccacc    4620
tgacgtctaa gaaaccatta ttatcatgac attaacctat aaaaataggc gtatcacgag    4680
gccctttcgt cttcac                                                   4696
```

<210> SEQ ID NO 10

<211> LENGTH: 4637
<212> TYPE: DNA
<213> ORGANISM: Artificial Sequence
<220> FEATURE:
<223> OTHER INFORMATION: pSCT5_DsbC/scvhFGF19

<400> SEQUENCE: 10

| | | | | | |
|---|---|---|---|---|---|
| ctcgagaaat | cataaaaaat | ttatttgctt | tgtgagcgga | taacaattat | aatagattca | 60 |
| attgtgagcg | ataacaatt | tcacacagaa | ttcattaaag | aggagaaaac | tagtatggat | 120 |
| gacgcggcaa | ttcaacaaac | gttagccaaa | atgggcatca | aaagcagcga | tattcagccc | 180 |
| gcgcctgtag | ctggcatgaa | gacagttctg | actaacagcg | gcgtgttgta | catcaccgat | 240 |
| gatggtaaac | atatcattca | ggggccaatg | tatgacgtta | gtggcacggc | tccggtcaat | 300 |
| gtcaccaata | gatgctgtt | aaagcagttg | aatgcgcttg | aaaagagat | gatcgtttat | 360 |
| aaagcgccgc | aggaaaaaca | cgtcatcacc | gtgtttactg | atattacctg | tggttactgc | 420 |
| cacaaactgc | atgagcaaat | ggcagactac | aacgcgctgg | ggatcaccgt | gcgttatctt | 480 |
| gctttcccgc | gccaggggct | ggacagcgat | gcagagaaaa | aaatgaaagc | tatctggtgt | 540 |
| gcgaaagata | aaaacaaagc | gtttgatgat | gtgatggcag | gtaaaagcgt | cgcaccagcc | 600 |
| agttgcgacg | tggatattgc | cgaccattac | gcacttggcg | tccagcttgg | cgttagcggt | 660 |
| actccggcag | ttgtgctgag | caatggcaca | cttgttccgg | gttaccagcc | gccgaaagag | 720 |
| atgaaagaat | tcctcgacga | acaccaaaaa | atgaccagcg | gtaaataagg | atccatgcga | 780 |
| cctctagcct | tttccgatgc | gggacctcac | gtgcactacg | gctggggcga | ccccatccgc | 840 |
| ctgcggcacc | tgtacacctc | cggccccac | gggctctcca | gctgcttcct | gcgcatccgt | 900 |
| gccgacggcg | tcgtggactg | cgcgcggggc | cagagcgcgc | acagtttgct | ggagatcaag | 960 |
| gcagtcgctc | tgcggaccgt | ggccatcaag | ggcgtgcaca | gcgtgcggta | cctctgcatg | 1020 |
| ggcgccgacg | gcaagatgca | ggggctgctt | cagtactcgg | aggaagactg | tgctttcgag | 1080 |
| gaggagatcc | gcccagatgg | ctacaatgtg | taccgatccg | agaagcaccg | cctcccggtc | 1140 |
| tccctgagca | gtgccaaaca | gcggcagctg | tacaagaaca | gaggctttct | tccactctct | 1200 |
| catttcctgc | ccatgctgcc | catggtccca | gaggagcctg | aggacctcag | gggccacttg | 1260 |
| gaatctgaca | tgttctcttc | gcccctggag | accgacagca | tggacccatt | tgggcttgtc | 1320 |
| accggactgg | aggccgtgag | gagtcccagc | tttgagaagt | aaaagcttaa | ttagctgagc | 1380 |
| ttggactcct | gttgatagat | ccagtaatga | cctcagaact | ccatctggat | tgttcagaa | 1440 |
| cgctcggttg | ccgccgggcg | ttttttattg | gtgagaatcc | aagctagctt | ggcgagattt | 1500 |
| tcaggagcta | aggaagctaa | aatggagaaa | aaaatcactg | gatataccac | cgttgatata | 1560 |
| tcccaatggc | atcgtaaaga | acattttgag | gcatttcagt | cagttgctca | atgtacctat | 1620 |
| aaccagaccg | ttcagctgga | tattacggcc | tttttaaaga | ccgtaaagaa | aaataagcac | 1680 |
| aagttttatc | cggcctttat | tcacattctt | gcccgcctga | tgaatgctca | tccggaattt | 1740 |
| cgtatggcaa | tgaaagacgg | tgagctggtg | atatgggata | gtgttcaccc | ttgttacacc | 1800 |
| gttttccatg | agcaaactga | aacgttttca | tcgctctgga | gtgaatacca | cgacgatttc | 1860 |
| cggcagtttc | tacacatata | ttcgcaagat | gtggcgtgtt | acggtgaaaa | cctggcctat | 1920 |
| ttccctaaag | ggtttattga | gaatatgttt | ttcgtctcag | ccaatccctg | ggtgagtttc | 1980 |
| accagttttg | atttaaacgt | ggccaatatg | gacaacttct | tcgcccccgt | tttcaccatg | 2040 |
| ggcaaatatt | atacgcaagg | cgacaaggtg | ctgatgccgc | tggcgattca | ggttcatcat | 2100 |
| gccgtttgtg | atggcttcca | tgtcggcaga | atgcttaatg | aattacaaca | gtactgcgat | 2160 |

```
gagtggcagg gcggggcgta attttttta ggcagttatt ggtgcccttta aacgcctggg      2220 gtaatgactc tctagcttga ggcatcaaat aaaacgaaag gctcagtcga aagactgggc      2280
ctttcgtttt atctgttgtt tgtcggtgaa cgctctcctg agtaggacaa atccgccctc      2340
tagagctgcc tcgcgcgttt cggtgatgac ggtgaaaacc tctgacacat gcagctcccg      2400
gagacggtca cagcttgtct gtaagcggat gccgggagca gacaagcccg tcagggcgcg      2460
tcagcgggtg ttggcgggtg tcggggcgca gccatgaccc agtcacgtag cgatagcgga      2520
gtgtatactg gcttaactat gcggcatcag agcagattgt actgagagtg caccatatgc      2580
ggtgtgaaat accgcacaga tgcgtaagga gaaaataccg catcaggcgc tcttccgctt      2640
cctcgctcac tgactcgctg cgctcggtcg ttcggctgcg gcgagcggta tcagctcact      2700
caaaggcggt aatacggtta tccacagaat caggggataa cgcaggaaag aacatgtgag      2760
caaaaggcca gcaaaaggcc aggaaccgta aaaaggccgc gttgctggcg ttttttccata      2820 ggctccgccc ccctgacgag catcacaaaa atcgacgctc aagtcagagg tggcgaaacc      2880
cgacaggact ataaagatac caggcgtttc cccctggaag ctccctcgtg cgctctcctg      2940
ttccgaccct gccgcttacc ggatacctgt ccgcctttct cccttcggga agcgtggcgc      3000
tttctcatag ctcacgctgt aggtatctca gttcggtgta ggtcgttcgc tccaagctgg      3060
gctgtgtgca cgaacccccc gttcagcccg accgctgcgc cttatccggt aactatcgtc      3120
ttgagtccaa cccggtaaga cacgacttat cgccactggc agcagccact ggtaacagga      3180
ttagcagagc gaggtatgta ggcggtgcta cagagttctt gaagtggtgg cctaactacg      3240
gctacactag aaggacagta tttggtatct gcgctctgct gaagccagtt accttcggaa      3300
aaagagttgg tagctcttga tccggcaaac aaaccaccgc tggtagcggt ggtttttttg      3360
tttgcaagca gcagattacg cgcagaaaaa aaggatctca agaagatcct ttgatctttt      3420
ctacggggtc tgacgctcag tggaacgaaa actcacgtta agggattttg gtcatgagat      3480
tatcaaaaag gatcttcacc tagatccttt taaattaaaa atgaagtttt aaatcaatct      3540
aaagtatata tgagtaaact tggtctgaca gttaccaatg cttaatcagt gaggcaccta      3600
tctcagcgat ctgtctattt cgttcatcca tagttgcctg actccccgtc gtgtagataa      3660
ctacgatacg ggagggctta ccatctggcc ccagtgctgc aatgataccg cgagacccac      3720
gctcaccggc tccagattta tcagcaataa accagccagc cggaagggcc gagcgcagaa      3780
gtggtcctgc aactttatcc gcctccatcc agtctattaa ttgttgccgg gaagctagag      3840
taagtagttc gccagttaat agtttgcgca acgttgttgc cattgctaca ggcatcgtgg      3900
tgtcacgctc gtcgtttggt atggcttcat tcagctccgg ttcccaacga tcaaggcgag      3960
ttacatgatc ccccatgttg tgcaaaaaag cggttagctc cttcggtcct ccgatcgttg      4020
tcagaagtaa gttggccgca gtgttatcac tcatggttat ggcagcactg cataattctc      4080
ttactgtcat gccatccgta agatgctttt ctgtgactgg tgagtactca accaagtcat      4140
tctgagaata gtgtatgcgg cgaccgagtt gctcttgccc ggcgtcaata cgggataata      4200
ccgcgccaca tagcagaact ttaaaagtgc tcatcattgg aaaacgttct cggggcgaa      4260 aactctcaag gatcttaccg ctgttgagat ccagttcgat gtaacccact cgtgcaccca      4320
actgatcttc agcatctttt actttcacca gcgtttctgg gtgagcaaaa acaggaaggc      4380
aaaatgccga aaaaaggga ataagggcga cacggaaatg ttgaatactc atactcttcc      4440
tttttcaata ttattgaagc atttatcagg gttattgtct catgagcgga tacatatttg      4500
```

| | |
|---|---:|
| aatgtattta gaaaaataaa caaatagggg ttccgcgcac atttccccga aaagtgccac | 4560 |
| ctgacgtcta agaaaccatt attatcatga cattaaccta taaaaatagg cgtatcacga | 4620 |
| ggccctttcg tcttcac | 4637 |

<210> SEQ ID NO 11
<211> LENGTH: 5165
<212> TYPE: DNA
<213> ORGANISM: Artificial Sequence
<220> FEATURE:
<223> OTHER INFORMATION: pACYCDuet1_DsbC/scvhFGF19

<400> SEQUENCE: 11

| | |
|---|---:|
| ggggaattgt gagcggataa caattcccct gtagaaataa ttttgtttaa ctttaataag | 60 |
| gagatatacc atggatggat gacgcggcaa ttcaacaaac gttagccaaa atgggcatca | 120 |
| aaagcagcga tattcagccc cgcctgtag ctggcatgaa gacagttctg actaacagcg | 180 |
| gcgtgttgta catcaccgat gatggtaaac atatcattca ggggccaatg tatgacgtta | 240 |
| gtggcacggc tccggtcaat gtcaccaata agatgctgtt aaagcagttg aatgcgcttg | 300 |
| aaaaagagat gatcgtttat aaagcgccgc aggaaaaaca cgtcatcacc gtgtttactg | 360 |
| atattacctg tggttactgc cacaaactgc atgagcaaat ggcagactac aacgcgctgg | 420 |
| ggatcaccgt gcgttatctt gctttcccgc gccaggggct ggacagcgat gcagagaaag | 480 |
| aaatgaaagc tatctggtgt gcgaaagata aaaacaaagc gtttgatgat gtgatggcag | 540 |
| gtaaaagcgt cgcaccagcc agttgcgacg tggatattgc cgaccattac gcacttggcg | 600 |
| tccagcttgg cgttagcggt actccggcag ttgtgctgag caatggcaca cttgttccgg | 660 |
| gttaccagcc gccgaaagag atgaaagaat cctcgacga acaccaaaaa atgaccagcg | 720 |
| gtaaataagg atccgaattc gagctcggcg cgcctgcagg tcgacaagct tgcggccgca | 780 |
| taatgcttaa gtcgaacaga agtaatcgt attgtacacg gccgcataat cgaaattaat | 840 |
| acgactcact atagggggaat tgtgagcgga taacaattcc ccatcttagt atattagtta | 900 |
| agtataagaa ggagatatac atatgcgacc tctagccttt tccgatgcgg gacctcacgt | 960 |
| gcactacggc tggggcgacc ccatccgcct gcggcacctg tacacctccg gcccccacgg | 1020 |
| gctctccagc tgcttcctgc gcatccgtgc cgacggcgtc gtggactgcg cgcggggcca | 1080 |
| gagcgcgcac agtttgctgg agatcaaggc agtcgctctg cggaccgtgg ccatcaaggg | 1140 |
| cgtgcacagc gtgcggtacc tctgcatggg cgccgacggc aagatgcagg ggctgcttca | 1200 |
| gtactcggag gaagactgtg ctttcgagga ggagatccgc ccagatggct acaatgtgta | 1260 |
| ccgatccgag aagcaccgcc tcccggtctc cctgagcagt gccaaacagc ggcagctgta | 1320 |
| caagaacaga ggctttcttc cactctctca tttcctgccc atgctgccca tggtcccaga | 1380 |
| ggagcctgag gacctcaggg gccacttgga atctgacatg ttctcttcgc ccctggagac | 1440 |
| cgacagcatg gacccatttg gcttgtcac cggactggag gccgtgagga gtcccagctt | 1500 |
| tgagaagtaa ctcgagtctg gtaaagaaac cgctgctgcg aaatttgaac gccagcacat | 1560 |
| ggactcgtct actagcgcag cttaattaac ctaggctgct gccaccgctg agcaataact | 1620 |
| agcataaccc cttggggcct ctaaacgggt cttgagggg ttttttgctga aacctcaggc | 1680 |
| atttgagaag cacacggtca cactgcttcc ggtagtcaat aaaccggtaa accagcaata | 1740 |
| gacataagcg gctatttaac gaccctgccc tgaaccgacg accgggtcga atttgctttc | 1800 |
| gaatttctgc cattcatccg cttattatca cttattcagg cgtagcacca ggcgtttaag | 1860 |
| ggcaccaata actgccttaa aaaaattacg ccccgccctg ccactcatcg cagtactgtt | 1920 |

```
gtaattcatt aagcattctg ccgacatgga agccatcaca gacggcatga tgaacctgaa   1980
tcgccagcgg catcagcacc ttgtcgcctt gcgtataata tttgcccata gtgaaaacgg   2040
gggcgaagaa gttgtccata ttggccacgt ttaaatcaaa actggtgaaa ctcacccagg   2100
gattggctga gacgaaaaac atattctcaa taaacccttt agggaaatag gccaggtttt   2160
caccgtaaca cgccacatct tgcgaatata tgtgtagaaa ctgccggaaa tcgtcgtggt   2220
attcactcca gagcgatgaa aacgtttcag tttgctcatg gaaaacggtg taacaagggt   2280
gaacactatc ccatatcacc agctcaccgt ctttcattgc catacggaac tccggatgag   2340
cattcatcag gcgggcaaga atgtgaataa aggccggata aaacttgtgc ttattttct    2400 ttacggtctt taaaaaggcc gtaatatcca gctgaacggt ctggttatag gtacattgag   2460
caactgactg aaatgcctca aaatgttctt tacgatgcca tgggatata tcaacggtgg    2520 tatatccagt gatttttttc tccattttag cttccttagc tcctgaaaat ctcgataact   2580
caaaaaatac gcccggtagt gatcttattt cattatggtg aaagttggaa cctcttacgt   2640
gccgatcaac gtctcatttt cgccaaaagt tggcccaggg cttcccggta tcaacaggga   2700
caccaggatt tatttattct gcgaagtgat cttccgtcac aggtatttat tcggcgcaaa   2760
gtgcgtcggg tgatgctgcc aacttactga tttagtgtat gatggtgttt ttgaggtgct   2820
ccagtggctt ctgtttctat cagctgtccc tcctgttcag ctactgacgg ggtggtgcgt   2880
aacggcaaaa gcaccgccgg acatcagcgc tagcggagtg tatactggct tactatgttg   2940
gcactgatga gggtgtcagt gaagtgcttc atgtggcagg agaaaaaagg ctgcaccggt   3000
gcgtcagcag aatatgtgat acaggatata ttccgcttcc tcgctcactg actcgctacg   3060
ctcggtcgtt cgactgcggc gagcggaaat ggcttacgaa cggggcggag atttcctgga   3120
agatgccagg aagatactta acaggaagt gagagggccg cggcaaagcc gttttccat    3180 aggctccgcc cccctgacaa gcatcacgaa atctgacgct caaatcagtg gtggcgaaac   3240
ccgacaggac tataaagata ccaggcgttt ccctggcgg ctccctcgtg cgctctcctg    3300
ttcctgcctt tcggtttacc ggtgtcattc cgctgttatg gccgcgtttg tctcattcca   3360
cgcctgacac tcagttccgg gtaggcagtt cgctccaagc tggactgtat gcacgaaccc   3420
cccgttcagt ccgaccgctg cgccttatcc ggtaactatc gtcttgagtc caacccggaa   3480
agacatgcaa aagcaccact ggcagcagcc actggtaatt gatttagagg agttagtctt   3540
gaagtcatgc gccggttaag gctaaactga aaggacaagt tttggtgact gcgctcctcc   3600
aagccagtta cctcggttca aagagttggt agctcagaga accttcgaaa aaccgccctg   3660
caaggcggtt ttttcgtttt cagagcaaga gattacgcgc agaccaaaac gatctcaaga   3720
agatcatctt attaatcaga taaaatattt ctagatttca gtgcaattta tctcttcaaa   3780
tgtagcacct gaagtcagcc ccatacgata aagttgtaa ttctcatgtt agtcatgccc    3840
cgcgcccacc ggaaggagct gactgggttg aaggctctca agggcatcgg tcgagatccc   3900
ggtgcctaat gagtgagcta acttacatta attgcgttgc gctcactgcc cgctttccag   3960
tcgggaaacc tgtcgtgcca gctgcattaa tgaatcggcc aacgcgcggg gagaggcggt   4020
ttgcgtattg ggcgccaggg tggtttttct tttcaccagt gagacgggca acagctgatt   4080
gcccttcacc gcctggccct gagagagttg cagcaagcgg tccacgctgg tttgccccag   4140
caggcgaaaa tcctgtttga tggtggttaa cggcgggata taacatgagc tgtcttcggt   4200
atcgtcgtat cccactaccg agatgtccgc accaacgcgc agcccggact cggtaatggc   4260
```

```
gcgcattgcg cccagcgcca tctgatcgtt ggcaaccagc atcgcagtgg gaacgatgcc    4320
ctcattcagc atttgcatgg tttgttgaaa accggacatg gcactccagt cgccttcccg    4380
ttccgctatc ggctgaattt gattgcgagt gagatattta tgccagccag ccagacgcag    4440
acgcgccgag acagaactta atgggcccgc taacagcgcg atttgctggt gacccaatgc    4500
gaccagatgc tccacgccca gtcgcgtacc gtcttcatgg gagaaaataa tactgttgat    4560
gggtgtctgg tcagagacat caagaaataa cgccggaaca ttagtgcagg cagcttccac    4620
agcaatggca tcctggtcat ccagcggata gttaatgatc agcccactga cgcgttgcgc    4680
gagaagattg tgcaccgccg ctttacaggc ttcgacgccg cttcgttcta ccatcgacac    4740
caccacgctg gcacccagtt gatcggcgcg agatttaatc gccgcgacaa tttgcgacgg    4800
cgcgtgcagg gccagactgg aggtggcaac gccaatcagc aacgactgtt tgcccgccag    4860
ttgttgtgcc acgcggttgg gaatgtaatt cagctccgcc atcgccgctt ccactttttc    4920
ccgcgttttc gcagaaacgt ggctggcctg gttcaccacg cgggaaacgg tctgataaga    4980
gacaccggca tactctgcga catcgtataa cgttactggt ttcacattca ccaccctgaa    5040
ttgactctct tccgggcgct atcatgccat accgcgaaag gttttgcgcc attcgatggt    5100
gtccgggatc tcgacgctct cccttatgcg actcctgcat taggaaatta atacgactca    5160
ctata                                                                 5165

<210> SEQ ID NO 12
<211> LENGTH: 5520
<212> TYPE: DNA
<213> ORGANISM: Artificial Sequence
<220> FEATURE:
<223> OTHER INFORMATION: pQHDuet_DsbC/scvhFGF19

<400> SEQUENCE: 12
ctcgagaaat cataaaaaat ttatttgctt tgtgagcgga taacaattat aatagattca      60
attgtgagcg gataacaatt tcacacagaa ttcattaaag aggagaaatt aactatggat     120
gacgcggcaa ttcaacaaac gttagccaaa atgggcatca aaagcagcga tattcagccc     180
gcgcctgtag ctggcatgaa gacagttctg actaacagcg gcgtgttgta catcaccgat     240
gatggtaaac atatcattca ggggccaatg tatgacgtta gtggcacggc tccggtcaat     300
gtcaccaata agatgctgtt aaagcagttg aatgcgcttg aaaagagat gatcgtttat     360 aaagcgccgc aggaaaaaca cgtcatcacc gtgtttactg atattacctg tggttactgc     420
cacaaactgc atgagcaaat ggcagactac aacgcgctgg gatcaccgt gcgttatctt     480 gctttcccgc gccaggggct ggacagcgat gcagagaaag aaatgaaagc tatctggtgt     540
gcgaaagata aaacaaagc gtttgatgat gtgatggcag gtaaaagcgt cgcaccagcc     600
agttgcgacg tggatattgc cgaccattac gcacttggcg tccagcttgg cgttagcggt     660
actccggcag ttgtgctgag caatggcaca cttgttccgg ttaccagcc gccgaaagag     720 atgaaagaat tcctcgacga acaccaaaaa atgaccagcg taaataagg atccgaattc     780 gagctcggcg cgcctgcagg tcgacaagct tgcggccgca taatgcttaa gtcgaacaga     840
aagtaatcgt attgtacacg gccgcataat cgaaattaat acgactcact ataggggaat     900
tgtgagcgga taacaattcc ccatcttagt atattagtta agtataagaa ggagatatac     960
atatgcgacc tctagccttt tccgatgcgg gacctcacgt gcactacggc tggggcgacc    1020
ccatccgcct gcggcacctg tacacctccg gcccccacgg gctctccagc tgcttcctgc    1080
gcatccgtgc cgacggcgtc gtggactgcg cgcggggcca gagcgcgcac agtttgctgg    1140
```

```
agatcaaggc agtcgctctg cggaccgtgg ccatcaaggg cgtgcacagc gtgcggtacc    1200
tctgcatggg cgccgacggc aagatgcagg ggctgcttca gtactcggag gaagactgtg    1260
ctttcgagga ggagatccgc ccagatggct acaatgtgta ccgatccgag aagcaccgcc    1320
tcccggtctc cctgagcagt gccaaacagc ggcagctgta caagaacaga ggctttcttc    1380
cactctctca tttcctgccc atgctgccca tggtcccaga ggagcctgag gacctcaggg    1440
gccacttgga atctgacatg ttctcttcgc ccctggagac cgacagcatg gacccatttg    1500
ggcttgtcac cggactggag gccgtgagga gtcccagctt tgagaagtaa ctcgagtctg    1560
gtaaagaaac cgctgctgcg aaatttgaac gccagcacat ggactcgtct actagcgcag    1620
cttaattaac ctaggctgct gccaccgctg agcaataact agcataaccc cttggggcct    1680
ctaaacgggt cttgaggggt ttttgctga aacctcaggc atttgagaag cacacggtca    1740
cactgcttcc ggtagtcaat aaaccggtaa accagcaata gacataagcg ctatttaac    1800 gaccctgccc tgaaccgacg accgggtcga atttgctttc gaatttctgc cattcatccg    1860
cttattatca cttattcagg cgtagcacca ggcgtttaag ggcaccaata actgccttaa    1920
aaaaaccgcc ctctagatta cgtgcagtcg atgataagct gtcaaacatg agaattgtgc    1980
ctaatgagtg agctaactta cattaattgc gttgcgctca ctgcccgctt tccagtcggg    2040
aaacctgtcg tgccagctgc attaatgaat cggccaacgc gcggggagag gcggtttgcg    2100
tattgggcgc cagggtggtt tttcttttca ccagtgagac gggcaacagc tgattgccct    2160
tcaccgcctg gccctgagag agttgcagca agcggtccac gctggtttgc cccagcaggc    2220
gaaaatcctg tttgatggtg gttaacggcg ggatataaca tgagctgtct tcggtatcgt    2280
cgtatcccac taccgagata tccgcaccaa cgcgcagccc ggactcggta atggcgcgca    2340
ttgcgcccag cgccatctga tcgttggcaa ccagcatcgc agtgggaacg atgccctcat    2400
tcagcatttg catggtttgt tgaaaaccgg acatggcact ccagtcgcct cccgttccg    2460 ctatcggctg aatttgattg cgagtgagat atttatgcca gccagccaga cgcagacgcg    2520
ccgagacaga acttaatggg cccgctaaca gcgcgatttg ctggtgaccc aatgcgacca    2580
gatgctccac gcccagtcgc gtaccgtctt catgggagaa aataatactg ttgatgggtg    2640
tctggtcaga gacatcaaga aataacgccg gaacattagt gcaggcagct tccacagcaa    2700
tggcatcctg gtcatccagc ggatagttaa tgatcagccc actgacgcgt tgcgcgagaa    2760
gattgtgcac cgccgcttta caggcttcga cgccgcttcg ttctaccatc gacaccacca    2820
cgctggcacc cagttgatcg cgcgcgagatt taatcgccgc gacaatttgc gacggcgcgt    2880
gcagggccag actggaggtg gcaacgccaa tcagcaacga ctgtttgccc gccagttgtt    2940
gtgccacgcg gttgggaatg taattcagct ccgccatcgc cgcttccact ttttcccgcg    3000
ttttcgcaga aacgtggctg gcctggttca ccacgcggga aacggtctga taagagacac    3060
cggcatactc tgcgacatcg tataacgtta ctggtttcac attcaccacc ctgaattgac    3120
tctcttccgg cgctatcat gccataccgc gaaaggtttt gcaccattcg atggtgtcgg    3180
aatttcgggc agcgttgggt cctggccacg ggtgcgcatg atctagagct gcctcgcgcg    3240
tttcggtgat gacggtgaaa acctctgaca catgcagctc ccgagacgg tcacagcttg    3300 tctgtaagcg gatgccggga gcagacaagc ccgtcagggc gcgtcagcgg gtgttggcgg    3360
gtgtcggggc gcagccatga cccagtcacg tagcgatagc ggagtgtata ctggcttaac    3420
tatgcggcat cagagcagat tgtactgaga gtgcaccata tgcggtgtga ataccgcac    3480
```

```
agatgcgtaa ggagaaaata ccgcatcagg cgctcttccg cttcctcgct cactgactcg      3540
ctgcgctcgg tcgttcggct gcggcgagcg gtatcagctc actcaaaggc ggtaatacgg      3600
ttatccacag aatcagggga taacgcagga agaacatgt gagcaaaagg ccagcaaaag       3660
gccaggaacc gtaaaaaggc cgcgttgctg gcgttttcc ataggctccg ccccctgac        3720 gagcatcaca aaatcgacg ctcaagtcag aggtggcgaa acccgacagg actataaaga      3780
taccaggcgt ttccccctgg aagctccctc gtgcgctctc ctgttccgac cctgccgctt     3840
accggatacc tgtccgcctt tctcccttcg ggaagcgtgg cgctttctca tagctcacgc      3900
tgtaggtatc tcagttcggt gtaggtcgtt cgctccaagc tgggctgtgt gcacgaaccc     3960
cccgttcagc ccgaccgctg cgccttatcc ggtaactatc gtcttgagtc caacccggta     4020
agacacgact tatcgccact ggcagcagcc actggtaaca ggattagcag agcgaggtat     4080
gtaggcggtg ctacagagtt cttgaagtgg tggcctaact acggctacac tagaaggaca     4140
gtatttggta tctgcgctct gctgaagcca gttaccttcg gaaaaagagt tggtagctct     4200
tgatccggca aacaaaccac cgctggtagc ggtggttttt tgtttgcaa gcagcagatt     4260 acgcgcagaa aaaaggatc tcaagaagat cctttgatct tttctacggg gtctgacgct      4320
cagtggaacg aaaactcacg ttaagggatt ttggtcatga gattatcaaa aaggatcttc     4380
acctagatcc ttttaaatta aaaatgaagt tttaaatcaa tctaaagtat atatgagtaa     4440
acttggtctg acagttacca atgcttaatc agtgaggcac ctatctcagc gatctgtcta     4500
tttcgttcat ccatagttgc ctgactcccc gtcgtgtaga taactacgat acgggagggc     4560
ttaccatctg gccccagtgc tgcaatgata ccgcgagacc cacgctcacc ggctccagat     4620
ttatcagcaa taaaccagcc agccggaagg gccgagcgca gaagtggtcc tgcaacttta     4680
tccgcctcca tccagtctat taattgttgc cgggaagcta gagtaagtag ttcgccagtt     4740
aatagtttgc gcaacgttgt tgccattgct acaggcatcg tggtgtcacg ctcgtcgttt     4800
ggtatggctt cattcagctc cggttcccaa cgatcaaggc gagttacatg atcccccatg     4860
ttgtgcaaaa aagcggttag ctccttcggt cctccgatcg ttgtcagaag taagttggcc     4920
gcagtgttat cactcatggt tatggcagca ctgcataatt ctcttactgt catgccatcc     4980
gtaagatgct tttctgtgac tggtgagtac tcaaccaagt cattctgaga atagtgtatg     5040
cggcgaccga gttgctcttg cccggcgtca tacgggata taccgcgcc acatagcaga      5100 actttaaaag tgctcatcat tggaaaacgt tcttcggggc gaaaactctc aaggatctta     5160
ccgctgttga tccagttc gatgtaaccc actcgtgcac ccaactgatc ttcagcatct       5220
tttactttca ccagcgtttc tgggtgagca aaaacaggaa ggcaaaatgc cgcaaaaaag     5280
ggaataaggg cgacacggaa atgttgaata ctcatactct cctttttca atattattga     5340 agcatttatc agggttattg tctcatgagc ggatacatat ttgaatgtat ttagaaaaat     5400
aaacaaatag gggttccgcg cacatttccc cgaaaagtgc cacctgacgt ctaagaaacc     5460
attattatca tgacattaac ctataaaaat aggcgtatca cgaggccctt tcgtcttcac     5520
```

<210> SEQ ID NO 13
<211> LENGTH: 27
<212> TYPE: DNA
<213> ORGANISM: Artificial Sequence
<220> FEATURE:
<223> OTHER INFORMATION: pSCT5_FGF19-mC-fw

<400> SEQUENCE: 13
ataactagta tgcgccccct cgccttc                                           27

<210> SEQ ID NO 14
<211> LENGTH: 52
<212> TYPE: DNA
<213> ORGANISM: Artificial Sequence
<220> FEATURE:
<223> OTHER INFORMATION: pSCT5_scvhFGF19-mC-fw
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 14
ataactagta tgcgnccnct ngcnttytcn gaygcnggnc cncacgtgca ct            52

<210> SEQ ID NO 15
<211> LENGTH: 33
<212> TYPE: DNA
<213> ORGANISM: Artificial Sequence
<220> FEATURE:
<223> OTHER INFORMATION: pSCT5_FGF19-mC-rv

<400> SEQUENCE: 15
ataggatccc ttctcaaagc tgggactcct cac                                 33

<210> SEQ ID NO 16
<211> LENGTH: 34
<212> TYPE: DNA
<213> ORGANISM: Artificial Sequence
<220> FEATURE:
<223> OTHER INFORMATION: pSCT5_scvhFGF19-rv

<400> SEQUENCE: 16
ataaagcttt tacttctcaa agctgggact cctc                                34

<210> SEQ ID NO 17
<211> LENGTH: 28
<212> TYPE: DNA
<213> ORGANISM: Artificial Sequence
<220> FEATURE:
<223> OTHER INFORMATION: pSCT5_ssDsbC-fw

<400> SEQUENCE: 17

```
ataactagta tggatgacgc ggcaattc                                          28
```

<210> SEQ ID NO 18
<211> LENGTH: 36
<212> TYPE: DNA
<213> ORGANISM: Artificial Sequence
<220> FEATURE:
<223> OTHER INFORMATION: pSCT5_ssDsbC-rv

<400> SEQUENCE: 18

```
ataggatcct tatttaccgc tggtcatttt ttggtg                                 36
```

<210> SEQ ID NO 19
<211> LENGTH: 34
<212> TYPE: DNA
<213> ORGANISM: Artificial Sequence
<220> FEATURE:
<223> OTHER INFORMATION: pSCT5_FGF19/ssDsbC-fw

<400> SEQUENCE: 19

```
ataggatcct aaatggatga cgcggcaatt caac                                   34
```

<210> SEQ ID NO 20
<211> LENGTH: 39
<212> TYPE: DNA
<213> ORGANISM: Artificial Sequence
<220> FEATURE:
<223> OTHER INFORMATION: pSCT5_FGF19/ssDsbC-rv

<400> SEQUENCE: 20

```
ataaagcttt tatttaccgc tggtcatttt ttggtgttc                              39
```

<210> SEQ ID NO 21
<211> LENGTH: 47
<212> TYPE: DNA
<213> ORGANISM: Artificial Sequence
<220> FEATURE:
<223> OTHER INFORMATION: pSCT5_scvhFGF19-fw

<400> SEQUENCE: 21

```
atacaatttc acacagaatt cattaaagag gagaaaggat ccatgcg                    47
```

<210> SEQ ID NO 22
<211> LENGTH: 34
<212> TYPE: DNA
<213> ORGANISM: Artificial Sequence
<220> FEATURE:
<223> OTHER INFORMATION: pSCT5_scvhFGF19-rv

<400> SEQUENCE: 22

```
ataaagcttt tacttctcaa agctgggact cctc                                   34
```

<210> SEQ ID NO 23
<211> LENGTH: 39
<212> TYPE: DNA
<213> ORGANISM: Artificial Sequence
<220> FEATURE:
<223> OTHER INFORMATION: pACYCDuet1_ssDsbC-fw

<400> SEQUENCE: 23

```
aggagatata ccatggatga cgcggcaatt caacaaacg                              39
```

<210> SEQ ID NO 24
<211> LENGTH: 39
<212> TYPE: DNA
<213> ORGANISM: Artificial Sequence
<220> FEATURE:
<223> OTHER INFORMATION: pACYCDuet1_ssDsbC-rv

<400> SEQUENCE: 24
ataggatcct tatttaccgc tggtcatttt ttggtgttc          39

<210> SEQ ID NO 25
<211> LENGTH: 41
<212> TYPE: DNA
<213> ORGANISM: Artificial Sequence
<220> FEATURE:
<223> OTHER INFORMATION: pACYCDuet1_scvhFGF19-fw

<400> SEQUENCE: 25
caatttcaca cagaattcat taaagaggag aaacatatgc g        41

<210> SEQ ID NO 26
<211> LENGTH: 37
<212> TYPE: DNA
<213> ORGANISM: Artificial Sequence
<220> FEATURE:
<223> OTHER INFORMATION: pACYCDuet1_scvhFGF19-rv

<400> SEQUENCE: 26
atactcgagt tacttctcaa agctgggact cctcacg            37

<210> SEQ ID NO 27
<211> LENGTH: 33
<212> TYPE: DNA
<213> ORGANISM: Artificial Sequence
<220> FEATURE:
<223> OTHER INFORMATION: pQE80L V-fw

<400> SEQUENCE: 27
agttaatttc tcctctttaa tgaattctgt gtg                33

<210> SEQ ID NO 28
<211> LENGTH: 20
<212> TYPE: DNA
<213> ORGANISM: Artificial Sequence
<220> FEATURE:
<223> OTHER INFORMATION: pQE80L V-rv

<400> SEQUENCE: 28 ccgcccctcta gattacgtgc                              20

<210> SEQ ID NO 29
<211> LENGTH: 34
<212> TYPE: DNA
<213> ORGANISM: Artificial Sequence
<220> FEATURE:
<223> OTHER INFORMATION: pQHDuet_Infu ssDsbC-fw

<400> SEQUENCE: 29
gaggagaaat taactatgga tgacgcggca attc               34

<210> SEQ ID NO 30
<211> LENGTH: 39
<212> TYPE: DNA
<213> ORGANISM: Artificial Sequence
<220> FEATURE:
<223> OTHER INFORMATION: pQHDuet_InfuFGF19-rv

<400> SEQUENCE: 30
taatctagag ggcggttttt aaggcagtta ttggtgccc          39

```
<210> SEQ ID NO 31
<211> LENGTH: 10
<212> TYPE: PRT
<213> ORGANISM: Homo sapiens

<400> SEQUENCE: 31

Arg Pro Leu Ala Phe Ser Asp Ala Gly Pro
1               5                   10

<210> SEQ ID NO 32
<211> LENGTH: 30
<212> TYPE: DNA
<213> ORGANISM: Homo sapiens

<400> SEQUENCE: 32 cgcccctcg ccttctcgga cgcggggccc                                        30

<210> SEQ ID NO 33
<211> LENGTH: 30
<212> TYPE: DNA
<213> ORGANISM: Artificial Sequence
<220> FEATURE:
<223> OTHER INFORMATION: scvFGF19
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 33
cgnccnctng cnttytcnga ygcnggnccn                                        30
```